(12) United States Patent
Miyagawa et al.

(10) Patent No.: US 7,117,738 B2
(45) Date of Patent: Oct. 10, 2006

(54) LIQUID LEVEL DETECTING APPARATUS

(75) Inventors: Isao Miyagawa, Kariya (JP); Atsushi Yasuda, Kariya (JP)

(73) Assignee: Denso Corporation, Kariya (JP)

( * ) Notice: Subject to any disclaimer, the term of this patent is extended or adjusted under 35 U.S.C. 154(b) by 132 days.

(21) Appl. No.: 10/952,852

(22) Filed: Sep. 30, 2004

(65) Prior Publication Data
US 2005/0284217 A1   Dec. 29, 2005

(30) Foreign Application Priority Data

| Oct. 2, 2003 | (JP) | ............................. 2003-344888 |
| Oct. 24, 2003 | (JP) | ............................. 2003-365106 |
| Oct. 28, 2003 | (JP) | ............................. 2003-367904 |
| Jan. 19, 2004 | (JP) | ............................. 2004-010954 |
| Jan. 19, 2004 | (JP) | ............................. 2004-010955 |
| Aug. 3, 2004 | (JP) | ............................. 2004-227003 |

(51) Int. Cl.
*G01F 23/00* (2006.01)
*G01F 23/28* (2006.01)

(52) U.S. Cl. ..................... 73/290 V; 73/642; 73/644

(58) Field of Classification Search .............. 73/290 V, 73/642, 644
See application file for complete search history.

(56) References Cited

U.S. PATENT DOCUMENTS 3,417,609 A * 12/1968 Graham ....................... 73/633
4,264,788 A * 4/1981 Keidel et al. ................ 310/334
5,119,676 A * 6/1992 Bower et al. ............. 73/290 V
5,159,838 A * 11/1992 Lynnworth .................... 73/644
5,319,973 A * 6/1994 Crayton et al. ........... 73/290 V
5,471,872 A * 12/1995 Cummings ................ 73/290 V
6,360,599 B1 * 3/2002 Pathak et al. ............. 73/290 V

FOREIGN PATENT DOCUMENTS

| JP | A-11-153471 | 6/1999 |
| JP | A-2001-208595 | 8/2001 |

* cited by examiner

*Primary Examiner*—Hezron Williams
*Assistant Examiner*—Samir Shah
(74) *Attorney, Agent, or Firm*—Posz Law Group, PLC

(57) ABSTRACT

A guide pipe is formed from a metal material, and its internal cross section has a circular shape whose diametric dimension gradually becomes smaller with a distance from an ultrasonic sensor. That is, the guide pipe is formed so that a route for transmitting an ultrasonic wave generated from the ultrasonic sensor may be tapered from this ultrasonic sensor toward a reflector plate. Thus, the acoustic pressure level of the ultrasonic wave which enters the reflector plate can be made higher than a value in a prior-art liquid level detecting apparatus. Accordingly, the energy of the ultrasonic wave generated from the ultrasonic sensor can be utilized for liquid level detection at a high efficiency, so that a fuel liquid level detecting apparatus capable of accurate liquid level detection can be provided.

7 Claims, 21 Drawing Sheets

LIQUID LEVEL DETECTING APPARATUS

CROSS REFERENCE TO RELATED APPLICATIONS

This application is based upon and claims the benefit of priority of: Japanese Patent Application No. 2003-344888 filed on Oct. 2, 2003; Japanese Patent Application No. 2003-365106 filed on Oct. 24, 2003; Japanese Patent Application No. 2003-367904 filed on Oct. 28, 2003; Japanese Patent Application No. 2004-010954 filed on Jan. 19, 2004; Japanese Patent Application No. 2004-010955 filed on Jan. 19, 2004; and Japanese Patent Application No. 2004-227003 filed on Aug. 3, 2004, the contents of which are incorporated herein by reference.

FIELD OF THE INVENTION

The present invention relates to a liquid level detecting apparatus for detecting the liquid surface height of a liquid within a tank, and it is well suited for use in, for example, detecting the liquid level of a fuel within a fuel tank which is mounted in an automobile.

BACKGROUND OF THE INVENTION

Heretofore, a liquid level detecting apparatus which detects the liquid surface level of a liquid within a tank has been, for example, one comprising an ultrasonic sensor which is installed in the fuel, and a reflector plate which is installed in the fuel and which turns an ultrasonic wave from the ultrasonic sensor toward the liquid level, wherein the ultrasonic wave reflected by the liquid level is received by the ultrasonic sensor through the reflector plate so as to calculate the liquid surface level (refer to, for example, JP11-153471A).

In the liquid level detecting apparatus stated above, a cylinder having a square internal cross section is fixed to a bottom surface within the fuel tank. The ultrasonic sensor is attached to one end side of the cylinder so as to be capable of generating the ultrasonic wave toward the other end side of the cylinder, while the reflector plate which turns the ultrasonic wave having proceeded inside the cylinder, toward the liquid level is disposed on the other end side of the cylinder. The cylinder forms an ultrasonic transmission route in the liquid level detecting apparatus.

In the prior-art liquid level detecting apparatus stated above, the cylinder is formed having the square internal cross section, and a uniform cross-sectional shape in the direction of the longitudinal axis of this cylinder. That is, among four wall surfaces which constitute the cylinder, two opposing ones are in a relationship in which they are parallel to each other.

The ultrasonic wave proceeds inside the cylinder while iterating reflections by the respective wall surfaces of the cylinder. Herein, each time the ultrasonic wave is reflected by the wall surface, it undergoes partial transmission through the wall surface, etc., so that the energy of the ultrasonic wave decreases gradually.

In the cylinder which is included in the prior-art liquid level detecting apparatus stated above, that is, in the cylinder whose cross-sectional shape is uniform in substantially the whole region thereof in the axial direction, the intensity of the ultrasonic wave entering the reflector plate, in other words, the acoustic pressure level of the ultrasonic wave per unit area in the cross section of the cylinder becomes lower than the acoustic pressure level of the ultrasonic wave in the vicinity of the ultrasonic sensor.

Therefore, the acoustic pressure level of the ultrasonic wave which is turned by the reflector plate toward the liquid level lowers. Consequently, the acoustic pressure level of the ultrasonic wave which is reflected by the liquid level lowers. Accordingly, it becomes difficult to detect the liquid level at a high accuracy.

Moreover, in a case where the fuel has quaked on account of the vibration of a vehicle, the travel thereof on a sloping road, or the like, the liquid level within the fuel tank comes above the cylinder and becomes slant especially when it is high. On this occasion, it is sometimes the case that the ultrasonic wave having proceeded inside the cylinder and arrived at the liquid level is reflected by this liquid level to proceed outside the cylinder, and that the reflected ultrasonic wave is not received by the ultrasonic sensor. Then, the problem occurs that the indicated value of a fuel indicator becomes unstable.

Further, in consideration of the fact that the velocity of an ultrasonic wave in a liquid changes depending upon the temperature, pressure, etc. of the liquid, there has been proposed a construction wherein an ultrasonic sensor is attached to the outside surface of the bottom of a liquid container so as to be capable of generating the ultrasonic wave toward the upper part of the interior of the container, and an ultrasonic reflector which turns the ultrasonic wave from the ultrasonic sensor, toward this ultrasonic sensor is installed at the position of a predetermined measurement reference height at the lower part of the interior of the container (refer to, for example, JP2001-208595A).

According to the construction, the ultrasonic sensor detects two sorts of data, namely, the round-trip time between the ultrasonic sensor and a liquid level and the round-trip time between the ultrasonic sensor and the reflector. Since the distance between the ultrasonic sensor and the reflector is known beforehand, the velocity of the ultrasonic wave in temperature and pressure conditions at that point of time can be directly and accurately calculated from the round-trip time between the ultrasonic sensor and the reflector. The position of the liquid level can be accurately detected from the ultrasonic velocity thus obtained, and the round-trip time between the ultrasonic sensor and the liquid level.

In the prior-art liquid level detecting apparatus stated above, however, the reflector is a component separate from the ultrasonic sensor, and it becomes difficult to keep the positional relationship of both the constituents highly accurate, because of the construction in which these constituents are fixed to the container. The accuracy of the positional relationship between the ultrasonic generation sensor and the ultrasonic reflector is greatly relevant to the measurement accuracy of the ultrasonic velocity in the liquid. Therefore, when the accuracy of the positional relationship between both the constituents lowers, the ultrasonic velocity in the liquid cannot be detected at a high accuracy, making it impossible to accurately detect the liquid level position.

SUMMARY OF THE INVENTION

An object of the present invention is to provide a liquid level detecting apparatus which can detect the height of a liquid surface accurately and stably.

A liquid level detecting apparatus according to the invention is constructed comprising an ultrasonic sensor, a reflector, a first cylinder and a second cylinder.

The ultrasonic sensor is installed at the bottom of a tank in which a liquid is stored, and it detects the position of a liquid level by generating an ultrasonic wave and receiving the ultrasonic wave reflected by the liquid level of the liquid.

The reflector turns the ultrasonic wave generated from the ultrasonic sensor, toward the liquid level.

The first cylinder encloses a first route which transmits the ultrasonic wave between the ultrasonic sensor and the reflector, and it is formed so that its internal sectional area in a plane perpendicular to the first route may gradually become smaller toward the reflector.

The second cylinder encloses a second route which transmits the ultrasonic wave between the reflector and the liquid level.

BRIEF DESCRIPTION OF THE DRAWINGS

Other features and advantages of the present invention will be appreciated, as well as methods of operation and the function of the related parts, from a study of the following detailed description, appended claims, and drawings, all of which form a part of this application. In the drawings:

DETAILED DESCRIPTION OF THE PREFERRED EMBODIMENTS

In each of the ensuing embodiments, the present invention will be described as a fuel liquid level detecting apparatus for detecting a fuel liquid level position in the fuel tank of an automobile.

(First Embodiment)

Figure 1:
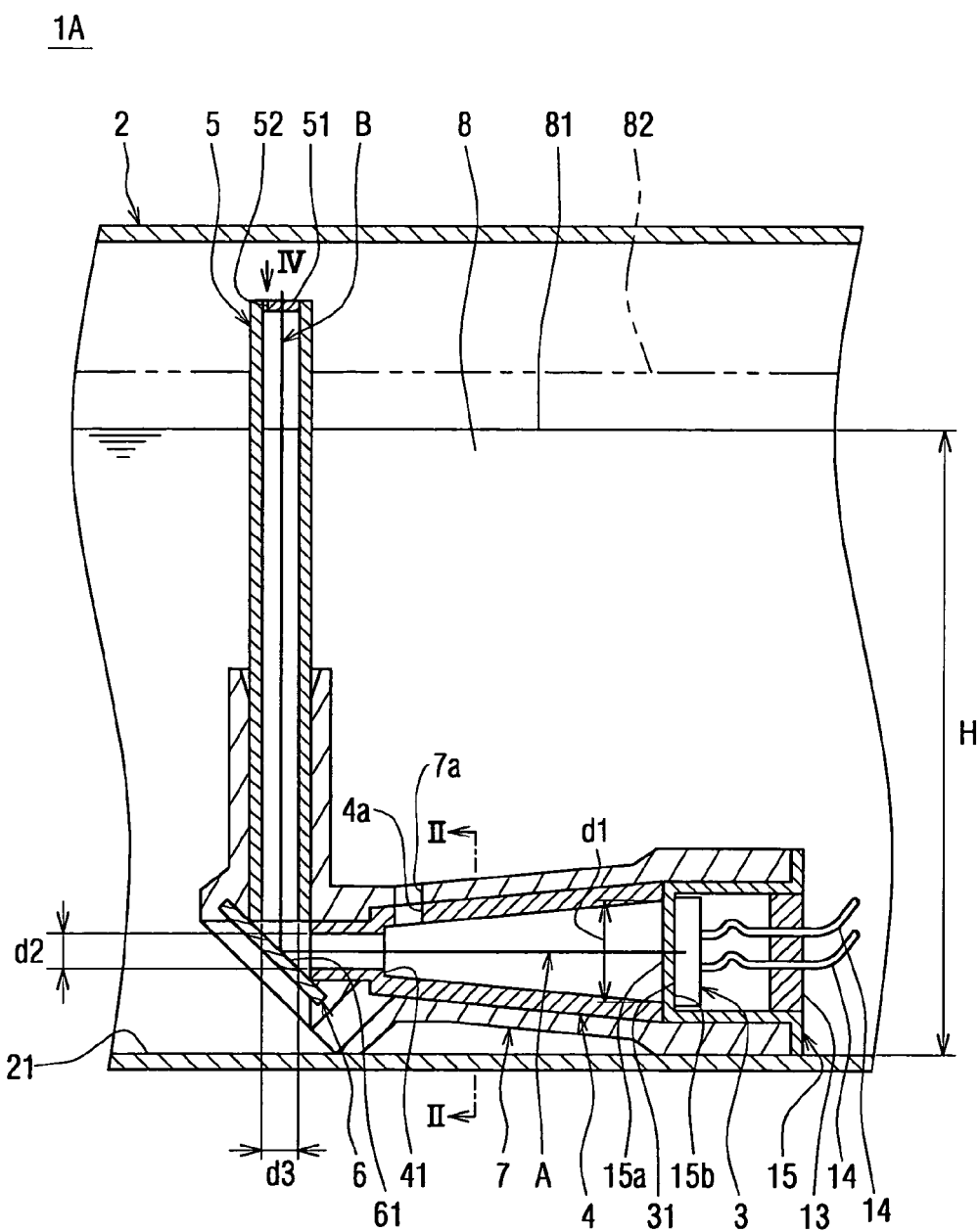
FIG. 1 is a partial sectional view of the first embodiment of a liquid level detecting apparatus according to the invention.

As shown in FIG. 1, a fuel liquid level detecting apparatus 1A includes a fuel tank 2, an ultrasonic sensor 3, a guide pipe (first cylinder) 4, a reflector plate 6, and a guide pipe (second cylinder) 5. Herein, the ultrasonic sensor 3, guide pipe 4, reflector plate 6 and guide pipe 5 are unitarily accommodated and held in a body 7, and they are attached to the bottom surface 21 of the fuel tank 2 through the body 7 as shown in FIG. 1.

The ultrasonic sensor 3 is installed on one end side of the guide pipe 4 in a state where the ultrasonic generation surface 31 thereof for generating an ultrasonic wave opposes to the interior of the guide pipe 4. That is, the ultrasonic sensor 3 is fixed to a bracket 15, and the bracket 15 is fitted in the body 7.

The ultrasonic sensor 3 is formed from a substance having a piezoelectric effect, for example, PZT (lead titanate zirconate). The ultrasonic sensor 3 has lead wires 14 for connection to an external electric circuit. The lead wires 14 are extended out of the bracket 15, and are further led out of the fuel tank 2 hermetically. Here, the "piezoelectric effect"

signifies the property that a volume is changed when a voltage is applied, while a voltage is generated when a force is received from outside.

The ultrasonic generation surface 31 of the ultrasonic sensor 3 is formed to be circular. When a pulse-shaped voltage is impressed on the ultrasonic sensor 3 through the lead wires 14, the ultrasonic generation surface 31 vibrates, whereby the ultrasonic wave is generated from the ultrasonic generation surface 31 into a fuel 8. On the other hand, when a reflected wave with the ultrasonic wave reflected by the liquid level of the fuel 8 arrives at the ultrasonic generation surface 31 to vibrate this ultrasonic generation surface 31 under the pressure action of the reflected wave, the ultrasonic sensor 3 generates a voltage, which is externally delivered as an output signal through the lead wires 14.

The bracket 15 is formed substantially in the shape of a bottomed cylinder from a resin or a metal, and the ultrasonic sensor 3 is fixed on the bottom 15b of the bracket 15 by, for example, bonding. A plug 13 is fixed on the open end side (right side in FIG. 1) of the bracket 15 by bonding, pressed fitting or the like. The plug 13 has the lead wires 14 inserted therethrough so as to hold them, and also prevents foreign matters from intruding into the bracket 15.

The bracket 15 is fixed on one end side (right side in FIG. 1) of the guide pipe 4 so that the ultrasonic generation surface 31 of the ultrasonic sensor 3 may face the other end (left side in FIG. 1) of the guide pipe 4, in other words, that the ultrasonic wave generated by the ultrasonic sensor 3 may be transmitted toward the other end side (left side in FIG. 1) within the guide pipe 4.

When the pulse-shaped voltage is impressed the ultrasonic sensor 3 through the lead wires 14, the ultrasonic generation surface 31 vibrates, and the vibration of the ultrasonic generation surface 31 is conveyed to the bottom 15b of the bracket 15. Further, the ultrasonic wave is generated from the outside surface 15a of the bracket 15 into the fuel 8. On the other hand, the ultrasonic wave is reflected by the liquid level 81 of the fuel 8 or the step 41 of the guide pipe 4, the reflected wave arrives at the ultrasonic generation surface 31 through the front surface 15a of the bracket 15, and the ultrasonic generation surface 31 vibrates under the pressure action of the reflected wave. Then, the ultrasonic sensor 3 generates the voltage, which is externally delivered as the output signal through the lead wires 14.

The guide pipe 4 which encloses the ultrasonic transmission route (first route) A between the ultrasonic sensor 3 and the reflector plate 6 is formed from an alloy for aluminum die casting, and one end side (right side in FIG. 1) of this guide pipe 4 is held in touch with the bracket 15 to which the ultrasonic sensor 3 is fixed.

Figure 2:
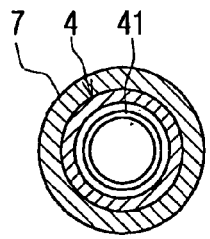
FIG. 2 is a sectional view taken along plane II—II in FIG. 1.

As shown in FIG. 2, the guide pipe 4 is formed so that a circular internal sectional shape may be defined in a direction perpendicular to the longitudinal axis A of this guide pipe 4, and that the internal sectional area of this guide pipe 4 in the direction perpendicular to the longitudinal axis A may gradually become smaller toward the reflector plate 6 (leftward in FIG. 1). More specifically, the guide pipe 4 has an internal diametric dimension d1 at its end near to the ultrasonic sensor 3 (right side in FIG. 1), while it has an internal diametric dimension d2 at its end near to the reflector plate 6 (left side in FIG. 1) (here, d1>d2 holds).

The guide pipe 4 and the body 7 are respectively formed with through holes 4a and 7a, which communicate with each other. The fuel 8 flows into the guide pipe 4 through the through holes 4a and 7a.

Besides, the guide pipe 4 is formed with the correcting reflective surface (step) 41. As shown in FIG. 2, the correcting reflective surface 41 is formed in the shape of a ring and as a surface opposing to the ultrasonic sensor 3. Accordingly, part of the ultrasonic wave generated from the ultrasonic sensor 3 enters the correcting reflective surface 41. The partial ultrasonic wave is reflected by the correcting reflective surface 41, and is received by the ultrasonic sensor 3.

Besides, the reflector plate 6 which turns the ultrasonic wave generated from the ultrasonic sensor 3, toward the liquid level 81 within the fuel tank 2, is installed on the side of the guide pipe 4 remote from the ultrasonic sensor 3 (left side in FIG. 1). The reflector plate 6 is formed of a stainless steel plate.

The reflector plate 6 turns the ultrasonic wave generated from the ultrasonic sensor 3 as has fallen on the reflective surface 61 of this reflector plate 6, toward the liquid level 81. More specifically, the reflector plate 6 is installed so as to turn the ultrasonic wave proceeding along the longitudinal axis A of the guide pipe 4, into a direction in which an incident angle on the liquid level 81 becomes zero degree, that is, into a direction which is perpendicular to the liquid level 81. In other words, the reflective surface 61 is located in a state where it is inclined 45 degrees relative to the liquid level 81.

The guide pipe 5 which encloses the ultrasonic transmission route (second route) B between the reflector plate 6 and the liquid level 81, is formed of a stainless steel tube. The sectional shape of the guide pipe 5 in a direction perpendicular to the longitudinal axis B thereof is formed to be circular, while the diameter of this guide pipe 5 has a diametric dimension d3 uniformly over the full length thereof. The diametric dimension d3 of the guide pipe 5 is made equal to the diametric dimension d2 of the guide pipe 4 at the end thereof on the side of the reflector plate 6.

A dashboard 51 is installed at the distal end of the guide pipe 5 remote from the reflector plate 6. When an automobile jolts during its travel on a bad road by way of example, the liquid level 81 within the fuel tank 2 consequently quakes to wave. On this occasion, when the wave flows into the guide pipe 5 through the opening of this guide pipe 5 on the upper end side thereof, the liquid level 81 temporarily rises, and hence, the accurate detection of the liquid level 81 becomes difficult. Therefore, the dashboard 51 as shown in FIG. 1 is installed at the distal end of the guide pipe 5. Thus, even when the automobile has jolted to give rise to the wave in the fuel tank 2, the flow of the fuel 8 into the guide pipe 5 can be prevented, and hence, the accurate detection of the liquid level 81 is permitted.

Figure 4:
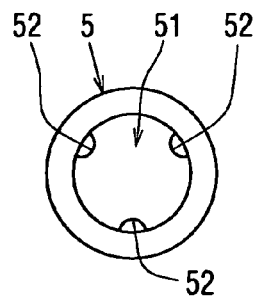
FIG. 4 is a view seen along arrow IV in FIG. 1.

The dashboard 51 is provided with notches 52 as shown in FIG. 4, whereby the air is permitted to communicate inside and outside the guide pipe 5. Accordingly, even when the dashboard 51 is installed, the liquid level 81 inside the guide pipe 5 can satisfactorily follow up the fluctuation of the liquid level 81 outside the guide pipe 5. Besides, as shown in FIG. 1, the distal end position of the guide pipe 5 on the side of the liquid level 81 is set so as to protrude a predetermined length above the liquid level 82 of the fuel 8 in the case where the storage quantity of the fuel 8 in the fuel tank 2 is the maximum, in other words, where the fuel tank 2 is full.

The bracket 15 for fixing the ultrasonic sensor 3 thereto, the guide pipe 4, the reflector plate 6 and the guide pipe 5 as described above, are installed on the body 7. The body 7 is formed from a resin material, for example, a resin material which exhibits an excellent stability against the fuel 8 in the fuel tank 2. The body 7 fulfills the functions of fixing the above constituent components while keeping their positional relationships highly accurate, and fixing the above constituent components on the bottom surface 21 of the fuel tank 2. Besides, the guide pipe 4, reflector plate 6 and guide pipe 5 in the state where they are fixed to the body 7 form a positional relationship in which the longitudinal axis A of the guide pipe 4 and that B of the guide pipe 5 intersect with each other on the reflective surface 61 of the reflector plate 6. Concretely, the bracket 15 for fixing the ultrasonic sensor 3 thereto, the guide pipe 4, the reflector plate 6 and the guide pipe 5 are assembled to the body 7.

Figure 3:
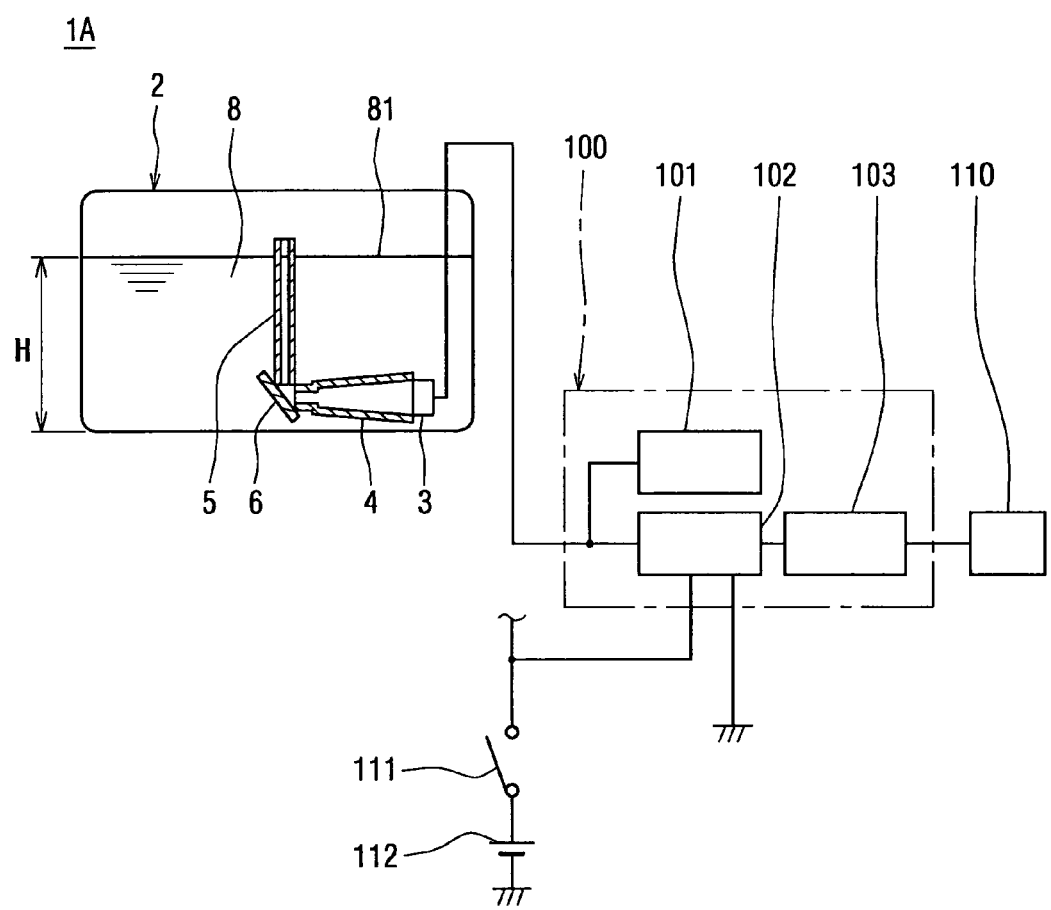
FIG. 3 is a schematic diagram showing an electric circuit arrangement in the first embodiment of the liquid level detecting apparatus according to the invention.

As shown in the block diagram of electric circuitry in FIG. 3, a control circuit 100 is connected to a battery 112 through an ignition switch 111. Besides, the control circuit 100 has the ultrasonic sensor 3 connected thereto. Also, the control circuit 100 has a display unit 110 connected thereto.

The control circuit 100 is constructed of, for example, a microcomputer, and it includes a pulse generation circuit 101 which applies a pulse-shaped voltage to the ultrasonic sensor 3, an arithmetic circuit 102 which processes a reflected-wave reception signal outputted from the ultrasonic sensor 3 and which calculates the position of the liquid level 81 on the basis of the reception signal, and a drive circuit 103 which outputs a drive signal for driving the display unit 110, on the basis of a liquid-level position signal calculated by the arithmetic circuit 102. When the control circuit 100 is fed with electric power from the battery 112 by the closure of the ignition switch 111, the fuel liquid level detecting apparatus 1A starts its operation.

The display unit 110 is constructed of, for example, a needle instrument or a liquid crystal panel, and it is installed in a combination meter (not shown) located in front of the driver seat of the automobile. The display unit 110 is driven by the drive circuit 103 of the control circuit 100, and it displays the position of the liquid level 81 calculated by the arithmetic circuit 102, in other words, the reserve or remaining quantity of the fuel 8 within the fuel tank 2 so as to be visually recognizable by the driver of the automobile.

Next, the operation of detecting the fuel liquid level by the fuel liquid level detecting apparatus 1A will be described.

When impressed with the pulse-shaped voltage signal by the pulse generation circuit 101, the ultrasonic sensor 3 generates a pulse-shaped ultrasonic wave into the fuel 8 within the fuel tank 2. Then, the ultrasonic generation surface 31 of the ultrasonic sensor 3 vibrates, the vibration of the ultrasonic generation surface 31 is conveyed to the bottom 15b of the bracket 15, and an ultrasonic wave is further generated from the outside surface 15a of the bracket 15 into the fuel 8. Part of this ultrasonic wave proceeds inside the guide pipe 4, and enters the correcting reflective surface 41. The partial ultrasonic wave is reflected by the correcting reflective surface 41, and it enters the ultrasonic generation surface 31 of the ultrasonic sensor 3 again. On the other hand, part of the pulse-shaped ultrasonic wave generated from the ultrasonic sensor 3 into the fuel 8 proceeds inside the guide pipe 4 and enters the reflective surface 61. The partial ultrasonic wave is reflected by the reflective surface 61, and it proceeds inside the guide pipe 5 and toward the liquid level 81. Further, it is reflected by the liquid level. 81, and it enters the ultrasonic sensor 3 along the same route as that of the going path, that is, via the guide pipe 5, reflective surface 61 and guide pipe 4.

Thus, when the ultrasonic sensor 3 is driven by the pulse generation circuit 101 to generate the single ultrasonic pulse, it receives the two reflected pulses; the reflected pulse from the correcting reflective surface 41 and the reflected pulse from the liquid level 81, in correspondence with the single-pulse generation as described above. As seen from FIG. 1, a transmission route length from the ultrasonic sensor 3 to the correcting reflective surface 41 is less than a transmission route length from the ultrasonic sensor 3 to the liquid level 81. Therefore, the ultrasonic sensor 3 first receives the reflected pulse from the correcting reflective surface 41 and subsequently receives the reflected pulse from the liquid level 81. When the ultrasonic sensor 3 receives the respective reflected pulses, it generates voltage signals, which are inputted to the arithmetic circuit 102.

The arithmetic circuit 102 calculates time periods which are expended since the issue of the pulse-shaped voltage signal by the pulse generation circuit 101, till the detections of the two reflected pulses stated above, respectively.

Here, the correcting reflective surface 41 is provided at a predetermined position relative to the ultrasonic sensor 3. That is, the distance between the correcting reflective surface 41 and the ultrasonic sensor 3 is known. Accordingly, the arithmetic circuit 102 calculates the propagation velocity of the ultrasonic pulse in the fuel 8, on the basis of the time period since the issue of the pulse-shaped voltage signal by the pulse generation circuit 101 till the reception of the reflected pulse from the correcting reflective surface 41, and the distance between the correcting reflective surface 41 and the ultrasonic sensor 3. Subsequently, the arithmetic circuit 102 calculates the position of the liquid level 81, namely, the height H of the liquid level 81 in FIG. 1, on the basis of the propagation velocity of the ultrasonic pulse in the fuel 8 as thus calculated, and the time period since the issue of the pulse-shaped voltage signal by the pulse generation circuit 101 till the reception of the reflected pulse from the liquid level 81. Further, the arithmetic circuit 102 calculates the reserve of the fuel 8 within the fuel tank 2, on the basis of the prestored shape of the fuel tank 2.

The drive circuit 103 outputs a signal for causing the display unit 110 to display the height H of the liquid level 81 or the reserve of the fuel 8 as calculated by the arithmetic circuit 102, for example, a drive signal for turning a needle shaft (not shown) up to an angle which corresponds to the height H of the liquid level 81 or the reserve of the fuel 8. Thus, the height H of the liquid level 81 in the fuel tank 2 or the reserve of the fuel 8 is displayed by the display unit 110.

Next, there will be described the construction and functional effects of the guide pipe 4 as form the characterizing features of the fuel liquid level detecting apparatus 1A.

In the fuel liquid level detecting apparatus 1A, the guide pipe 4 is formed from a metal material, namely, an aluminum die casting material. The internal section of the guide pipe 4 in a direction perpendicular to the longitudinal axis A thereof, that is, the internal cross-sectional shape is made circular, and the diametric dimension of the internal cross section of this guide pipe 4 is made smaller with a distance from the ultrasonic sensor 3. In other words, the guide pipe 4 is formed so that the ultrasonic transmission route may taper from the ultrasonic sensor 3 toward the reflector plate 6.

Thus, the degree of attenuation of ultrasonic energy as is involved while the ultrasonic wave generated from the ultrasonic sensor 3 proceeds to the reflector plate 6 inside the guide pipe 4 can be made lower than in case of the prior-art liquid level detecting apparatus, whereby the acoustic pressure level of the ultrasonic wave in the vicinity of the end of the guide pipe 4 on the side of the reflector plate 6, namely, the acoustic pressure level of the ultrasonic wave falling on the reflector plate 6 can be made higher than a level in the prior-art liquid level detecting apparatus. Accordingly, the energy of the ultrasonic wave generated from the ultrasonic sensor 3 can be utilized for the liquid level detection at a high efficiency, so that the fuel liquid level detecting apparatus 1A capable of the liquid level detection at a high accuracy can be provided.

Besides, in the fuel liquid level detecting apparatus 1A, the diametric dimension d2 of the end of the guide pipe 4 on the side of the reflector plate 6 is set to be equal to the diametric dimension d3 of the end of the guide pipe 5 on the side of the reflector plate 6.

On this occasion, in a case where the ultrasonic wave generated from the ultrasonic sensor 3 is transmitted from the guide pipe 4 into the guide pipe 5 via the reflector plate 6, and in a case where the ultrasonic wave reflected by the liquid level 81 is transmitted from the guide pipe 5 into the guide pipe 4 via the reflector plate 6, the cross-sectional areas of the transmission routes hardly change at the transitional part between the guide pipes 4 and 5. Accordingly, the energy losses of the ultrasonic waves are difficult to occur at the joint part between the guide pipes 4 and 5.

Besides, in the fuel liquid level detecting apparatus 1A, the guide pipe 5 is formed so as to have the uniform diametric dimension over the full length thereof.

Thus, the guide pipe 5 can be formed of, for example, a steel pipe being easily available, so that the cost of the fuel liquid level detecting apparatus 1A can be lowered. Besides, when the shape of the fuel tank 2 is altered in correspondence with the vehicle for mounting this fuel tank thereon, the height of the liquid level 82 of the fuel tank 2 in a full tank condition changes, and hence, the length of the guide pipe 5 needs to be changed correspondingly. In this case, with the construction in which the guide pipe 5 is formed of the steel pipe, the fuel liquid level detecting apparatus 1A corresponding to the fuel tank 2 of the different shape can be fabricated by the very simple expedient of altering the length of the guide pipe 5.

Besides, in the fuel liquid level detecting apparatus 1A, the guide pipes 4 and 5 are respectively formed from the metal materials.

The metal materials exhibit high reflection factors for the ultrasonic waves, in other words, they are difficult to transmit the ultrasonic waves therethrough. Therefore, when the guide pipes 4 and 5 are formed from the metal materials, the energy losses of the ultrasonic waves in the courses in which the ultrasonic waves proceed inside the guide pipes 4 and 5 are suppressed to the minima, whereby the energy of the ultrasonic wave generated from the ultrasonic sensor 3 can be utilized for the liquid level detection at a high efficiency.

By the way, in the fuel liquid level detecting apparatus 1A, the guide pipe 4 is formed from the aluminum die casting alloy, while the guide pipe 5 is formed of the stainless steel pipe. However, the guide pipes 4 and 5 need not be restricted to these metal materials, but other kinds of metal materials may well be employed. By way of example, it is also allowed to form the guide pipe 4 from a steel material, and to form the guide pipe 5 out of an aluminum pipe. Further, the guide pipes 4 and 5 may well be formed from substances other than the metal materials, for example, resin materials or ceramics materials. Any materials may be used as long as they can efficiently transmit the ultrasonic waves.

Besides, the fuel liquid level detecting apparatus 1A is constructed in such a manner that the bracket 15 with the ultrasonic sensor 3 fixed thereto, the guide pipe 4, the reflector plate 6 and the guide pipe 5 are assembled to the body 7. However, the detecting apparatus 1A need not be restricted to such a construction, but it may well be constructed, for example, in such a way that, at the resin molding of the body 7, the guide pipe 4, reflector plate 6 and guide pipe 5 are simultaneously formed by insert molding, whereupon the bracket 15 with the ultrasonic sensor 3 fixed thereto is assembled to the body 7.

Besides, the fuel liquid level detecting apparatus 1A is constructed in such a manner that the guide pipe 4, guide pipe 5 and reflector plate 6 are formed as the components independent of one another, and that they are assembled to the body 7. However, at least two of the guide pipe 4, guide pipe 5 and reflector plate 6 may well be unitarily formed as a single component. In this case, it is also allowed to omit the body 7, and to fix the unitary component to the fuel tank 2 through the remaining one of the guide pipe 4, guide pipe 5 and reflector plate 6.

Besides, although the guide pipe 4 is provided with the correcting reflective surface 41 in the fuel liquid level detecting apparatus 1A, the correcting reflective surface 41 need not be especially formed. In this case, by way of example, the temperature of the fuel 8 within the fuel tank 2 is detected by a temperature sensor (not shown) or the like, and the height H of the liquid level 81 is calculated by correcting the ultrasonic propagation velocity in the fuel 8 on the basis of the detected temperature, whereby the height H of the liquid level 81 can be calculated at a high accuracy.

(Second Embodiment)

Figure 5:
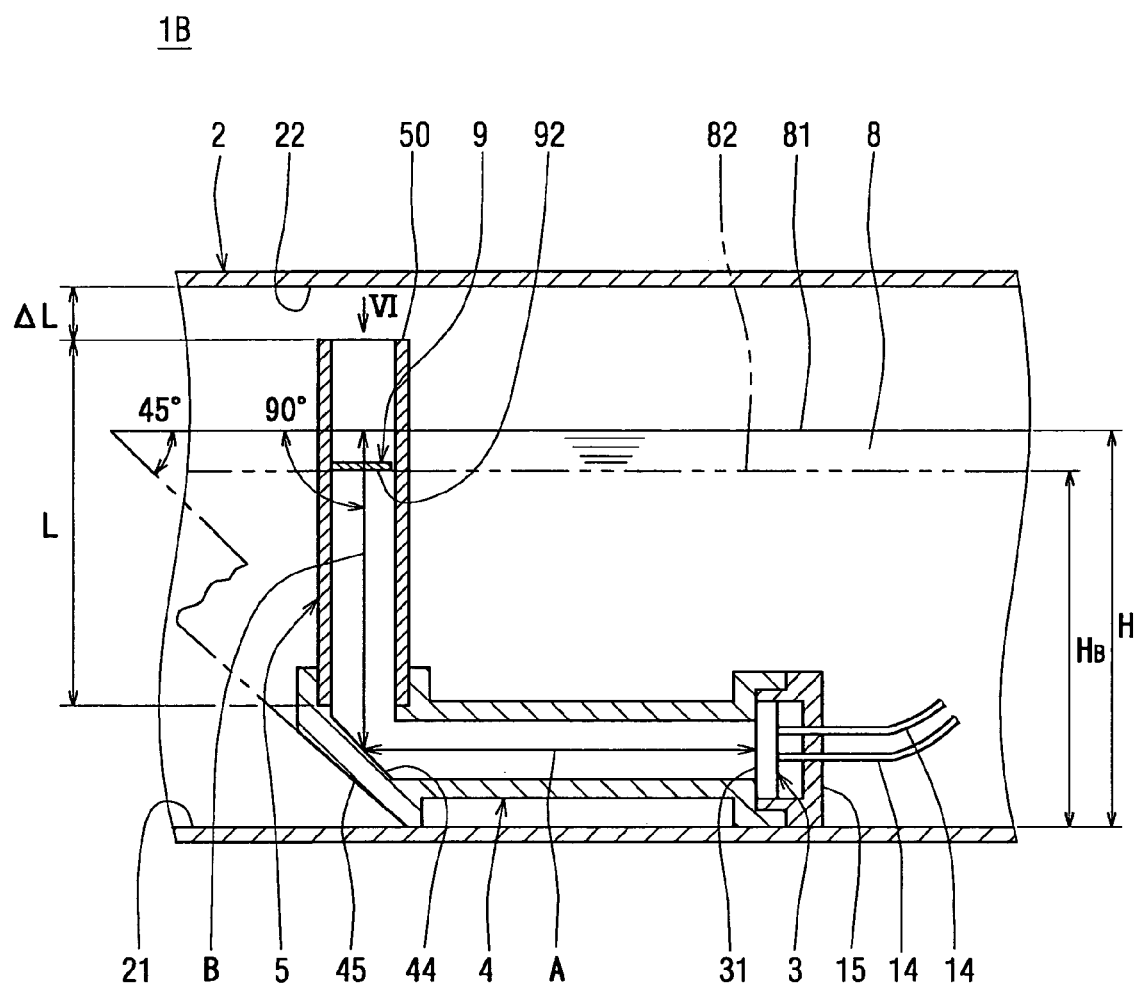
FIG. 5 is a partial sectional view of the second embodiment of the liquid level detecting apparatus according to the invention.

As shown in FIG. 5, a fuel liquid level detecting apparatus 1B in a second embodiment is such that the guide pipe (first cylinder) 4 of the fuel liquid level detecting apparatus 1A in the first embodiment is altered into a shape to be stated later, and that a baffle plate 9 is installed in the guide pipe (second cylinder) 5 instead of the dashboard 51. Besides, the bracket 15 of the fuel liquid level detecting apparatus 1B is such that the bracket 15 and the plug 13 fitted therein in the fuel liquid level detecting apparatus 1A of the first embodiment, are unitarily formed. The other constituents of the fuel liquid level detecting apparatus 1B are constructed similarly to the corresponding constituents of the fuel liquid level detecting apparatus 1A, respectively.

The guide pipe 4 is formed in the shape of a cylinder of uniform sectional shape from an aluminum die casting alloy. An ultrasonic sensor 3 is attached to one end side of the guide pipe 4 (right side in FIG. 5) through the bracket 15. The ultrasonic sensor 3 and the guide pipe 4 are coaxially installed.

A reflector plate (reflector) 45 is formed unitarily with the guide pipe 4 on the other end side of the guide pipe 4 (left side in FIG. 5).

The guide pipe 5 is formed in a cylindrical shape, and is fixed on the side of the guide pipe 4 near to the reflector plate 45. This guide pipe 5 is formed of a stainless steel pipe, and it is fixed to the part of the guide pipe 4 corresponding to the reflector plate 45, by pressed fitting or the like. The full length dimension L of the guide pipe 5 is set so that the upper end 50 of this guide pipe 5 near to a liquid level 81 may protrude above the highest liquid level 81 in the case where a fuel 8 is stored in a fuel tank 2 in the maximum storage quantity, namely, where the fuel tank 2 is full, and that a clearance ΔL may be defined between the upper end 50 and the ceiling inside surface 22 of the fuel tank 2.

Figure 6:
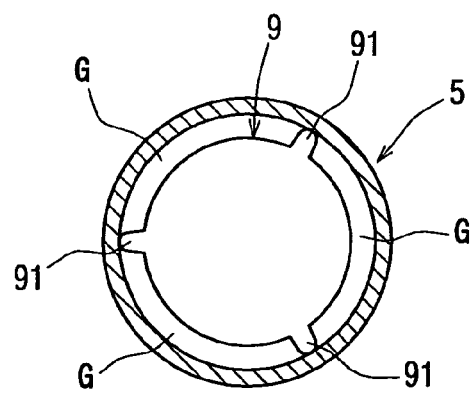
FIG. 6 is a view seen along arrow VI in FIG. 5.
Figure 7:
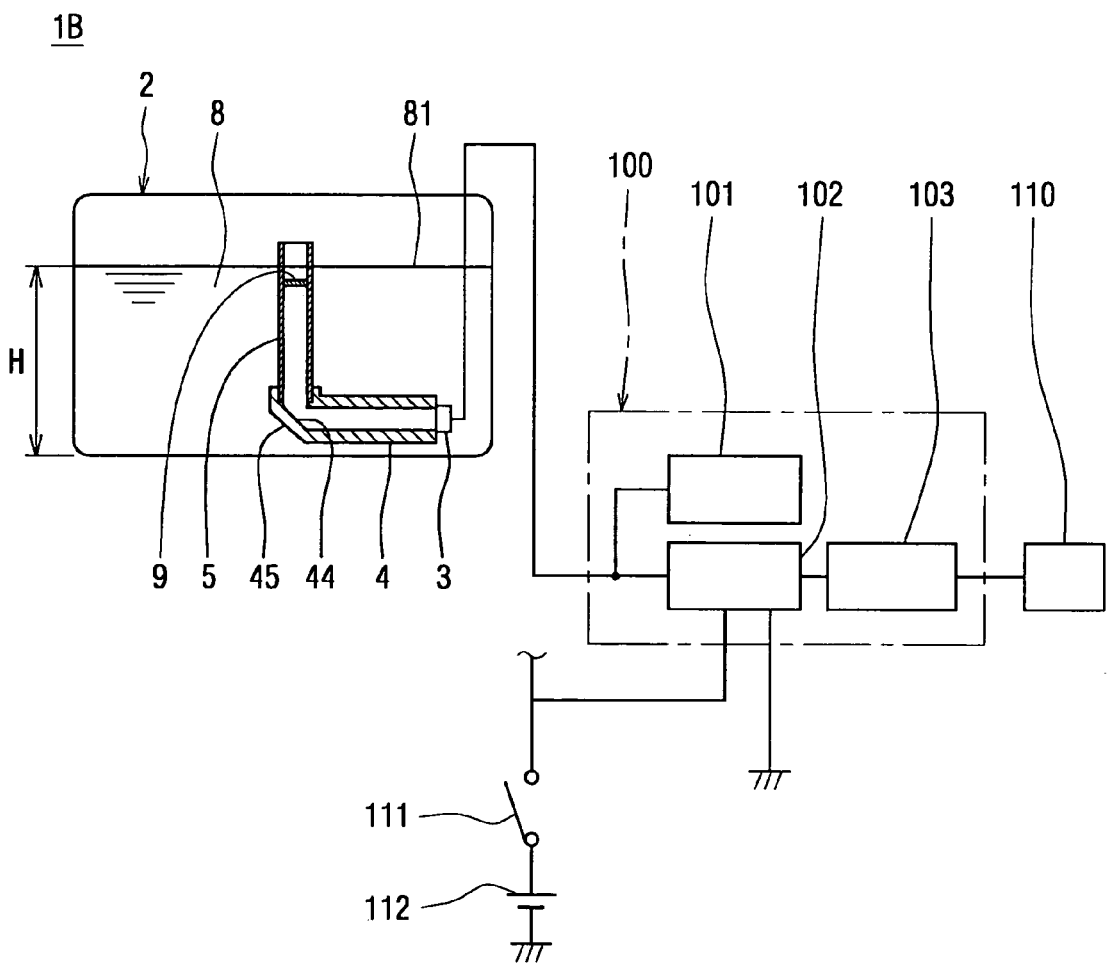
FIG. 7 is a schematic diagram showing an electric circuit arrangement in the second embodiment of the liquid level detecting apparatus according to the invention.

The baffle plate 9 being a partition plate is attached within the guide pipe 5. This baffle plate 9 is formed from a metal material such as aluminum plate, by press work or the like. As shown in FIG. 6, the baffle plate 9 is such that three protuberances 91 are provided at intervals of 120 degrees on the outer periphery of a small disc whose diameter is smaller than the inside diameter of the guide pipe 5.

The diameter of the circumscribed circle of the three protuberances 91 of the baffle plate 9 is set to be slightly larger than the inside diameter of the guide pipe 5. Accordingly, when the baffle plate 9 is pressedly fitted from the side of the upper end 50 into the guide pipe 5, this guide pipe 5 and the protuberances 91 are elastically deformed, and their restoring forces fix the baffle plate 9 rigidly inside the guide pipe 5. When the baffle plate 9 has been fixed inside the guide pipe 5, gaps G in the shape of circular arcs, in other words, passages communicating the front side and back side of the baffle plate 9, are defined between the guide pipe 5 and the baffle plate 9 as shown in FIG. 6. Since the front side and back side of the baffle plate 9 are communicated by the gaps G, the liquid level 81 inside the guide pipe 5 changes in interlocking with the fluctuation of the liquid level 81 outside the guide pipe 5. Accordingly, the position of the liquid level 81 within the fuel tank 2 can be accurately detected by the fuel liquid level detecting apparatus 1B.

The baffle plate 9 is fixed inside the guide pipe 5 in such a manner that a liquid level 82 in the case where a fuel storage quantity within the fuel tank 2 corresponds to 90% of the maximum storage quantity coincides with the lower surface 92 of the baffle plate 9, and that the lower surface 92 is parallel to the liquid level 81. The baffle plate 9 covers a region including the center of the guide pipe 5, in a state where it is fixed inside the guide pipe 5.

The operations of detecting the fuel liquid level by the fuel liquid level detecting apparatus 1B will be described chiefly on the functional effects of the baffle plate 9 installed in the guide pipe 5.

(1) Case where the fuel liquid level 81 within the fuel tank 2 lies between the liquid level 81 corresponding to the full tank condition and the liquid level 82 corresponding to the 90%-storage quantity, that is, where the fuel liquid level 81 lies above the lower surface 92 of the baffle plate 9:

In this case, an ultrasonic pulse generated from the ultrasonic sensor 3 reaches the lower surface 92 of the baffle plate 9 before reaching the liquid level 81, it is reflected by the lower surface 92, and the reflected ultrasonic pulse reaches the ultrasonic sensor 3 again via a transmission route B, a reflective surface 44 and a transmission route A, thereby to vibrate the ultrasonic generation surface 31 of the ultrasonic sensor 3. Thus, the ultrasonic sensor 3 generates a voltage signal, and the voltage signal, namely, a reflected-pulse detection signal is inputted to an arithmetic circuit 102.

More specifically, in the case where the position of the fuel liquid level 81 lies between the liquid level 81 corresponding to the full tank condition and the liquid level 82 corresponding to the 90%-storage quantity, a time period which is expended since the issue of a pulse-shaped voltage signal by a pulse generation circuit 101 till the detection of the voltage signal based on the reflected pulse, always becomes a constant value. On this occasion, a liquid level height which is calculated by the arithmetic circuit 102 is the height HB of the baffle plate 9. Accordingly, a fuel reserve which is indicated on a display unit 110 is always the maximum quantity.

Here, when the fuel 8 within the fuel tank 2 has quaked due to the jolting of an automobile during the travel thereof, it is sometimes the case that the liquid level 81 comes above the upper end 50 of the guide pipe 5, and that it inclines relative to a horizontal direction.

In the absence of the baffle plate 9, when the ultrasonic wave which proceeds from the reflective surface 44 toward the liquid level 81 by tracing the transmission route B is reflected by the liquid level 81, the reflected wave proceeds outside the guide pipe 5 without passing through the transmission route B. That is, the reflected wave from the liquid level 81 is not received by the ultrasonic sensor 3. Therefore, the arithmetic circuit 102 fails to accurately calculate the fuel reserve, and a fuel reserve display by the display unit 110 becomes unstable. As a concrete example, in a case where the display unit 110 is a needle instrument, there occurs the drawback that a needle turns unsteadily between a full tank (F) indication and an empty (E) indication.

In contrast, according to the fuel liquid level detecting apparatus 1B, the reflected wave from the baffle plate 9 is received by the ultrasonic sensor 3 without fail, and hence, the fuel reserve which is indicated on the display unit 110 is stable at the maximum quantity.

Thus, it is possible to obtain the fuel liquid level detecting apparatus 1B in which, when the liquid level 81 within the fuel tank 2 has inclined, the indicated value of the display unit 110 can be kept stable, thereby to afford an excellent visuality.

(2) Case where the position of the fuel liquid level 81 within the fuel tank 2 lies below the liquid level 82 corresponding to the 90%-storage quantity, that is, where it lies below the lower surface 92 of the baffle plate 9:

In this case, the ultrasonic pulse reaches the liquid level 81 before reaching the lower surface 92 of the baffle plate 9, it is reflected by the liquid level 81, and the reflected ultrasonic pulse reaches the ultrasonic sensor 3 again via the transmission route B, reflective surface 44 and transmission route A, thereby to vibrate the ultrasonic generation surface 31. Thus, the ultrasonic sensor 3 generates a voltage signal, and the voltage signal, namely, a reflected-pulse detection signal is inputted to the arithmetic circuit 102.

More specifically, in the case where the fuel liquid level 81 lies below the liquid level 82 corresponding to the 90%-storage quantity, a time period which is expended since the issue of the pulse-shaped voltage signal by the pulse generation circuit 101 till the detection of the voltage signal based on the reflected pulse, changes in correspondence with the position of the liquid level 81. On this occasion, the arithmetic circuit 102 calculates an actual liquid level height H. Further, it calculates a fuel reserve within the fuel tank 2, from the liquid level height H and a tank shape prestored as data. Besides, the fuel reserve is indicated on the display unit 110.

Here, when the fuel 8 within the fuel tank 2 has quaked due to the jolting of the automobile during the travel thereof, it is sometimes the case that the liquid level 81 comes above the upper end 50 of the guide pipe 5, and that it inclines relative to the horizontal direction.

In the absence of the baffle plate 9, when the ultrasonic wave which proceeds from the reflective surface 44 toward the liquid level 81 by tracing the transmission route B is reflected by the liquid level 81, the reflected wave proceeds outside the guide pipe 5 without passing through the transmission route B. That is, the reflected wave from the liquid level 81 is not received by the ultrasonic sensor 3. Therefore, the arithmetic circuit 102 fails to accurately calculate the fuel reserve, and the fuel reserve display by the display unit 110 becomes unstable. By way of example, in the case where the display unit 110 is the needle instrument, there occurs the drawback that the needle turns unsteadily between the full tank (F) indication and the empty (E) indication.

In contrast, according to the fuel liquid level detecting apparatus 1B, the reflected wave from the baffle plate 9 is received by the ultrasonic sensor 3 without fail, and hence, the display unit 110 stably indicates that the fuel reserve is the maximum quantity. In other words, although the needle moves from actual indicated values, it is stabilized at the maximum value. Accordingly, the driver of the automobile can readily judge that the movement of the needle is ascribable to the jolting of the automobile during the travel, so he/she can devote himself/herself to the drive of the automobile without feeling uneasy.

In general, when the fuel reserve is from the full tank condition of 100% of the storage capacity of the fuel tank 2, to about 90% of the storage capacity, the driver need not consider fuel replenishment or the like. Accordingly, even when the indicated value of the display unit 110 is fixed at the full tank indication, there is no problem.

On the other hand, when the fuel reserve has become less than 90%, the driver needs to determine a fuel replenishment time while considering the drive plan of the automobile. Accordingly, a high accuracy is required of that indicated value of the fuel reserve which is displayed on the display unit 110. The fuel liquid level detecting apparatus 1B can satisfactorily meet the requirement.

In the fuel liquid level detecting apparatus 1B described above, the guide pipe 5 is disposed in such a manner that the upper end 50 is extended above the liquid level 81 in the case where the storage quantity of the fuel 8 within the fuel tank 2 is the maximum quantity, and that the clearance $\Delta L$ is defined between the upper end 50 and the ceiling inside surface 22 of the fuel tank 2, and the baffle plate 9 is fixed inside the guide pipe 5 in such a manner that its lower surface 92 is substantially parallel to the liquid level 81, and that the lower surface 92 is held near the maximum liquid level 81, more particularly, in coincidence with the liquid level 82 in the case where the fuel storage quantity within the fuel tank 2 is 90% of the maximum storage quantity. Further, the gaps G which are the passages for communicating the front side and back side of the baffle plate 9 are formed between the baffle plate 9 and the guide pipe 5.

Thus, the attitude of the fuel liquid level detecting apparatus 1B can be easily changed within the fuel tank 2, so that the job of attaching the fuel liquid level detecting apparatus 1B into the fuel tank 2 can be performed with ease.

Besides, in the case where the fuel 8 in the fuel tank 2 has quaked due to the jolting of the automobile during the travel thereof and where the liquid level 81 has come above the upper end 50 of the guide pipe 5 and inclined relative to the horizontal direction, the liquid level detecting apparatus which is not provided with the baffle plate 9 undergoes the drawback that, since the reflected wave from the liquid level 81 proceeds outside the guide pipe 5 and cannot be received by the ultrasonic sensor 3, the arithmetic circuit 102 fails to accurately calculate the fuel reserve, so the fuel reserve display by the display unit 110 becomes unstable. In contrast, according to the fuel liquid level detecting apparatus 1B, the ultrasonic wave from the ultrasonic sensor 3 is reflected by the baffle plate 9, and the ultrasonic sensor 3 is permitted to reliably receive the reflected ultrasonic wave, whereby the fuel reserve display by the display unit 110 can be made the maximum quantity and be stably presented. Thus, it is possible to realize the fuel liquid level detecting apparatus 1B of excellent visuality in which the indicated value of the display unit 110 can be kept stable when the liquid level 81 within the fuel tank 2 has inclined.

Besides, in the fuel liquid level detecting apparatus 1B, the guide pipe 5 is installed to be substantially coaxial with the transmission route B being a reflection axis, namely, an axis along which the ultrasonic wave proceeding along the axis of the ultrasonic sensor 3, that is, the ultrasonic wave tracing the transmission route A is reflected by the reflective surface 44 so as to proceed toward the liquid level 81, and the baffle plate 9 covers the region including, at least, the center of the guide pipe 5.

The ultrasonic wave is conically radiated from the ultrasonic sensor 3, and the energy of the ultrasonic wave becomes the maximum in the axial direction of the ultrasonic sensor 3, that is, in the direction perpendicular to the ultrasonic sensor 3. Accordingly, the ultrasonic wave in the direction of the maximum energy is reliably reflected by the baffle plate 9, whereby when the liquid level 81 lies above the baffle plate 9, the energy of the ultrasonic wave reflected by the baffle plate 9 and entering the ultrasonic sensor 3 can be kept high to heighten the output signal level of the ultrasonic sensor 3.

Besides, in the fuel liquid level detecting apparatus 1B, the baffle plate 9 is formed as the component separate from the guide pipe 5 and is thereafter attached to the guide pipe 5.

In this manner, the baffle plate 9 and the guide pipe 5 are constructed as the separate components. Owing to the construction, in fabricating the fuel liquid level detecting apparatus 1B adapted to cope with a plurality of fuel tanks 2 which differ in the height H of the liquid level 81 in the condition of the maximum storage quantity of the fuel 8, the guide pipe 5 is used in common, and merely the position of the fixation of the baffle plate 9 to the guide pipe 5 is changed in correspondence with the respective fuel tanks 2, whereby a plurality of sorts of fuel liquid level detecting apparatuses 1B can be easily fabricated with cost rise suppressed.

(Modification to Second Embodiment)

Figure 8:
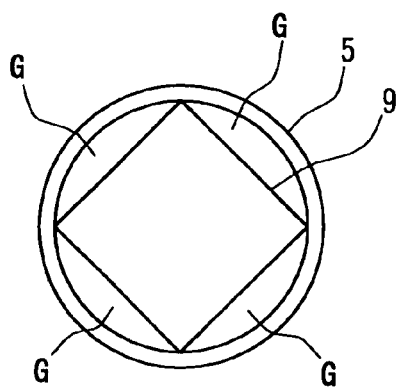
FIG. 8 is a plan view showing a modification of a baffle plate in the second embodiment of the liquid level detecting apparatus according to the invention.

In the modification of the baffle plate 9 as shown in FIG. 8, the baffle plate 9 is formed to be square. In this case, it is also allowed to employ a polygon different from the square, which has three or more apices.

Figure 9:
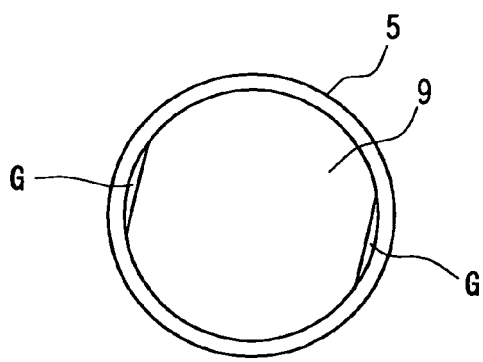
FIG. 9 is a plan view showing another modification of the baffle plate in the second embodiment of the liquid level detecting apparatus according to the invention.

In the other modification of the baffle plate 9 as shown in FIG. 9, the baffle plate 9 is in the shape of a circle, the two circumferential parts of which are cut away.

By the way, in the fuel liquid level detecting apparatus 1B, the guide pipe 4 is formed from the aluminum die casting alloy, while the guide pipe 5 is formed of the stainless steel pipe. However, the guide pipes 4 and 5 need not be restricted to these metal materials, but they may well be formed in a combination of other substances. Alternatively, they may well be formed from an identical substance. Further, the guide pipes 4 and 5 may well be formed as a unitary component.

Besides, in the fuel liquid level detecting apparatus 1B, the baffle plate 9 is formed by press work or the like out of an aluminum plate, but it may well be formed of another metal plate, for example, a brass or steel plate. Also, it may well be formed from a resin material.

Besides, in the fuel liquid level detecting apparatus 1B, the baffle plate 9 and the guide pipe 5 are formed as the separate members, but they may well be unitarily formed. By way of example, they may well be unitarily fabricated from the resin material or the aluminum die casting alloy.

Besides, in the fuel liquid level detecting apparatus 1B, the reflective surface 44 is shaped in a flat surface, but it may well be shaped in a concave surface which is concave facing both the ultrasonic generation surface 31 and the liquid level 81.

Besides, in the fuel liquid level detecting apparatus 1B, the guide pipe 4 is formed in the cylindrical shape whose sectional shape is substantially uniform, but the whole inside surface of the guide pipe 4 may well be formed in the shape of the conical surface as in the first embodiment, so as to heighten the acoustic pressure level of the ultrasonic wave entering the reflective surface 44.

Besides, the guide pipe 4 of the fuel liquid level detecting apparatus 1B may well be provided with the correcting reflective surface 41 as in the first embodiment, so as to compute the propagation velocity of the ultrasonic wave within the fuel 8 and to calculate the height of the liquid level 81 by utilizing the computed propagation velocity.

(Third Embodiment)

Figure 10:
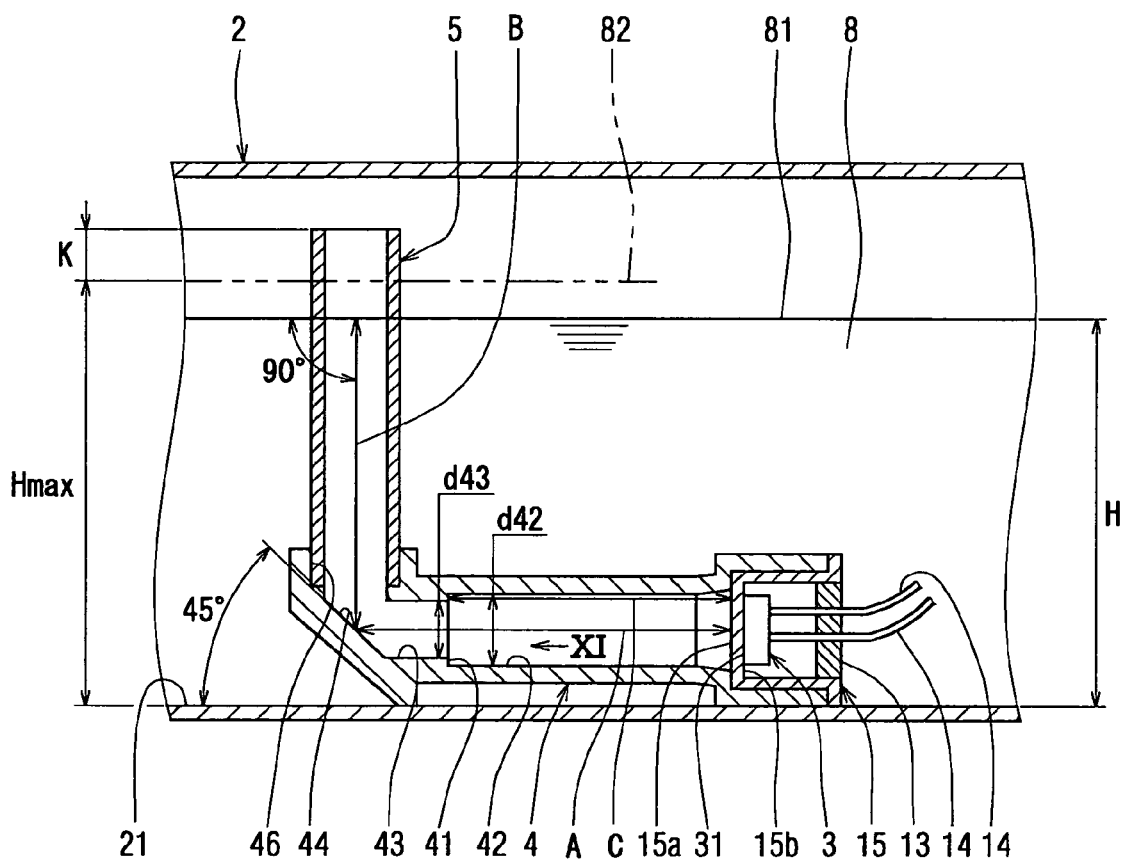
FIG. 10 is a partial sectional view of the third embodiment of the liquid level detecting apparatus according to the invention.
Figure 11:
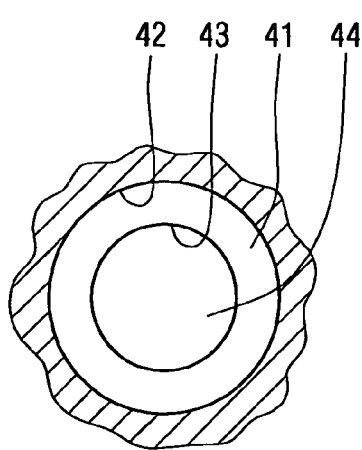
FIG. 11 is a view seen along arrow XI in FIG. 10.
Figure 12:
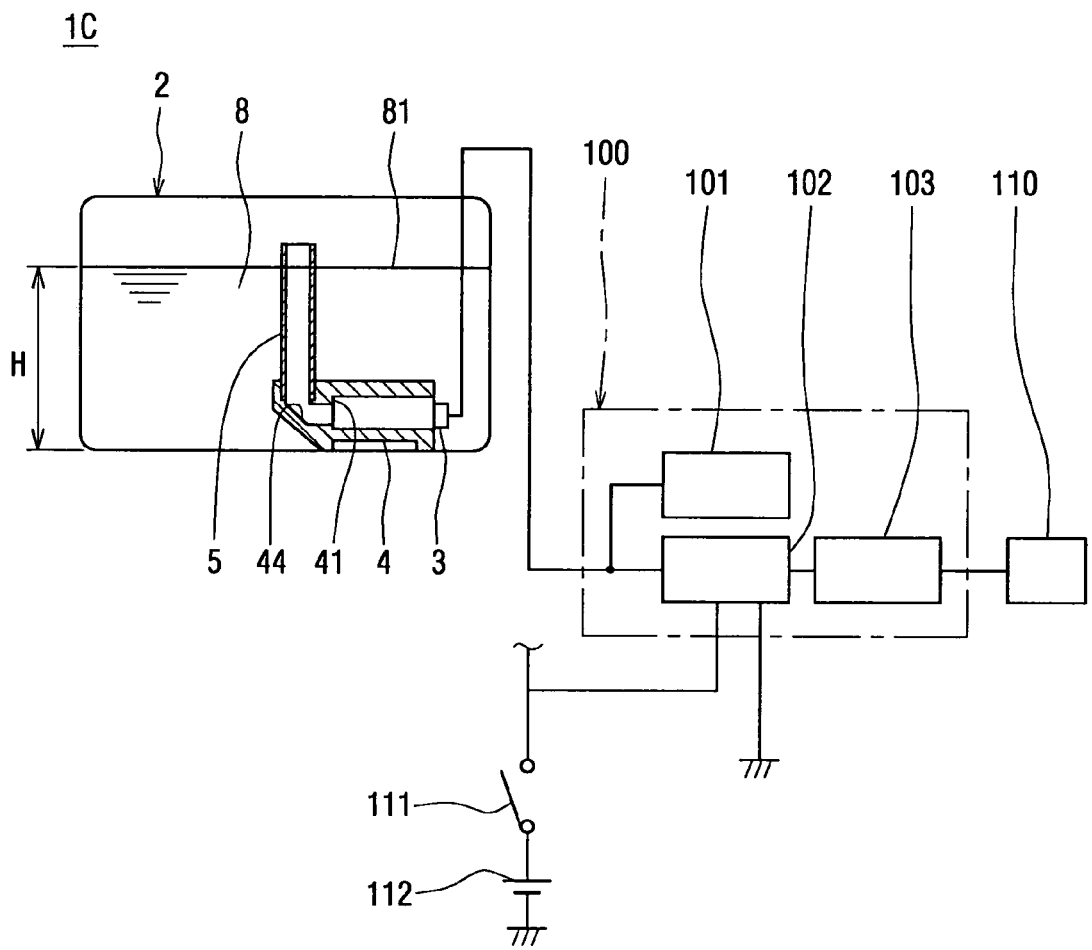
FIG. 12 is a schematic diagram showing an electric circuit arrangement in the third embodiment of the liquid level detecting apparatus according to the invention.

As shown in FIG. 10, a fuel liquid level detecting apparatus 1C in the third embodiment is such that a correcting reflective surface (step) 41 to be stated later is provided inside the guide pipe (first cylinder) 4 of the fuel liquid level detecting apparatus 1B in the second embodiment, and that the baffle plate 9 inside the guide pipe (second cylinder) 5 is omitted. Besides, likewise to the bracket 15 of the fuel liquid level detecting apparatus 1A in the first embodiment, the bracket 15 of the fuel liquid level detecting apparatus 1C is formed in the state where the plug 13 is fitted therein. The other constituents of the fuel liquid level detecting apparatus 1C are constructed similarly to the corresponding constituents of the fuel liquid level detecting apparatus 1B, respectively.

In the guide pipe 4, a large-diameter portion 42 and a small-diameter portion 43, which are cylindrical and which enclose the ultrasonic-wave transmission route (first route) A between an ultrasonic sensor 3 and a measuring reflective surface (reflector) 44, are located in the order of the large-diameter portion 42 and the small-diameter portion 43 as viewed from the side of the ultrasonic sensor 3. The diameter d42 of the large-diameter portion 42 is set to be larger than the diameter d43 of the small-diameter portion 43, and the large-diameter portion 42 and the small-diameter portion 43 are located coaxially with the ultrasonic generation surface 31 of the ultrasonic sensor 3.

The correcting reflective surface 41 is formed at the joint part between the large-diameter portion 42 and the small-diameter portion 43 so as to oppose to the ultrasonic sensor 3, in other words, perpendicularly to the traveling direction of an ultrasonic wave in the transmission route A. The correcting reflective surface 41 defines an annular shape in which the outside diameter d42 and the inside diameter d43 are coaxially located. Accordingly, part of the ultrasonic wave generated from the ultrasonic sensor 3 falls on the correcting reflective surface 41 by tracing a transmission route C which is part of the transmission route A, it is reflected there, and the reflected ultrasonic wave traces the transmission route C again and is received by the ultrasonic sensor 3.

The operation of detecting a fuel liquid level 81 in the fuel liquid level detecting apparatus 1C will be described.

When impressed with a pulse-shaped voltage signal by a pulse generation circuit 101, the ultrasonic sensor 3 generates a pulse-shaped ultrasonic wave into a fuel 8 within a fuel tank 2. Then, the ultrasonic generation surface 31 of the ultrasonic sensor 3 vibrates, the vibration of the ultrasonic generation surface 31 is conveyed to the bottom 15b of the bracket 15, and an ultrasonic wave is further generated from the outside surface 15a of the bracket 15 into the fuel 8. Part of this ultrasonic wave proceeds inside the guide pipe 4 by tracing the transmission route C shown in FIG. 10, and enters the correcting reflective surface 41. The partial ultrasonic wave is reflected there, and it enters the ultrasonic generation surface 31 of the ultrasonic sensor 3 again by tracing the transmission route C.

The remainder of the ultrasonic wave generated from the ultrasonic sensor 3 into the fuel 8 proceeds inside the guide pipe 4 by tracing the transmission route A and enters the measuring reflective surface 44. The remainder ultrasonic wave is reflected by the measuring reflective surface 44, and it proceeds inside a guide pipe 5 and toward the liquid level 81 by tracing a transmission route B. Further, it is reflected by the liquid level 81, and it enters the ultrasonic sensor 3 along the same route as that of the going path, that is, via the transmission route B, measuring reflective surface 44 and transmission route A again.

Thus, when the ultrasonic sensor 3 generates the single ultrasonic pulse, it receives the two reflected pulses; the reflected pulse from the correcting reflective surface 41 and the reflected pulse from the liquid level 81. The length of the transmission route C from the ultrasonic sensor 3 to the correcting reflective surface 41 is less than the length of a transmission route (A+B) from the ultrasonic sensor 3 to the liquid level 81. Therefore, the ultrasonic sensor 3 first receives the reflected pulse from the correcting reflective surface 41 and subsequently receives the reflected pulse from the liquid level 81. When the ultrasonic sensor 3 receives the respective reflected pulses, it generates voltage signals, which are inputted to an arithmetic circuit 102.

The arithmetic circuit 102 calculates time periods which are expended since the issue of the pulse-shaped voltage signal by the pulse generation circuit 101, till the detections of the two reflected pulses stated above, respectively.

The relative position of the correcting reflective surface 41 to the ultrasonic sensor 3 is fixed, and the distance between them is known. Accordingly, the arithmetic circuit 102 calculates the propagation velocity of the ultrasonic pulse within the fuel 8, on the basis of the time period since the issue of the pulse-shaped voltage signal by the pulse generation circuit 101 till the reception of the reflected pulse from the correcting reflective surface 41, and the distance between the correcting reflective surface 41 and the ultrasonic sensor 3.

Subsequently, the arithmetic circuit 102 calculates the height H of the liquid level 81, on the basis of the propagation velocity of the ultrasonic pulse within the fuel 8 as thus calculated, and the time period since the issue of the pulse-shaped voltage signal by the pulse generation circuit 101 till the reception of the reflected pulse from the liquid level 81. Further, the arithmetic circuit 102 calculates the reserve of the fuel 8 within the fuel tank 2, on the basis of the prestored shape of the fuel tank 2.

A drive circuit 103 outputs a signal for causing a display unit 110 to display the height H of the liquid level 81 or the reserve of the fuel 8 as calculated by the arithmetic circuit 102, for example, a drive signal for turning a needle shaft (not shown) up to an angle which corresponds to the height H of the liquid level 81 or the reserve of the fuel 8. Thus, the height H of the liquid level 81 in the fuel tank 2 or the reserve of the fuel 8 is displayed by the display unit 110.

In the fuel liquid level detecting apparatus 1C, the ultrasonic sensor 3 is directly fixed to the guide pipe 4 which is unitarily provided with the correcting reflective surface 41.

Accordingly, the relative position between the ultrasonic sensor 3 and the correcting reflective surface 41 is kept highly accurate, and the liquid level 81 of the fuel 8 can be detected at a high accuracy.

Besides, the correcting reflective surface 41 is formed in the annular shape in which the outside diameter d42 and the inside diameter d43 lie coaxially with the ultrasonic sensor 3.

In general, the energy distribution of an ultrasonic wave generated from the ultrasonic sensor 3 forms a shape of axial symmetry. Therefore, when the correcting reflective surface 41 is located coaxially with the ultrasonic sensor 3, a reflected wave, which develops in such a way that the ultrasonic wave generated from the ultrasonic sensor 3 is reflected by the reflective surface 41, comes to have an energy distribution in the shape of axial symmetry and is received by the ultrasonic sensor 3.

Thus, when the ultrasonic sensor 3 has received the reflected wave from the reflective surface 41, it can output a stable detection signal of high level, so that the ultrasonic propagation velocity within the fuel 8 can be detected at a high accuracy. Accordingly, the liquid level 81 of the fuel 8 can be detected at a high accuracy.

Besides, in the fuel liquid level detecting apparatus 1C, the reflective surface 44 which reflects the ultrasonic wave generated from the ultrasonic sensor 3, toward the liquid level 81, is provided at the end of the guide pipe 4 remote from the ultrasonic sensor 3, unitarily with this guide pipe 4.

Thus, the relative position between the ultrasonic sensor 3 and the measuring reflective surface 44, and an angle defined between the ultrasonic sensor 3 and the measuring reflective surface 44 are kept highly accurate, and the reflected wave reflected by the liquid level 81 can be received by the ultrasonic sensor 3 without fail, so as to reliably output the detection signal of the reflected wave from the liquid level 81.

Besides, the fuel liquid level detecting apparatus 1C includes the guide pipe 5 which encloses the ultrasonic transmission route B between the measuring reflective surface 44 and the liquid level 81, and which is fixed to the guide pipe 4.

Accordingly, the ultrasonic wave generated from the ultrasonic sensor 3 can be prevented from diffusing into the fuel tank 2 in the course in which it is reflected by the measuring reflective surface 44 so as to proceed toward the liquid level 81, or in the course in which it is reflected by the liquid level 81 so as to proceed toward the measuring reflective surface 44. Such diffusion lowers the reception level of the ultrasonic sensor 3. Besides, even when the liquid level 81 has quaked during the travel of an automobile, the fluctuation of the liquid level 81 inside the guide pipe 5 is suppressed to a low level. It is accordingly possible to suppress the fluctuation of that indicated value of the display 110 which indicates the height H of the liquid level 81 (the reserve of the fuel 8) within the fuel tank 2.

(Modification to Third Embodiment)

Figure 13:
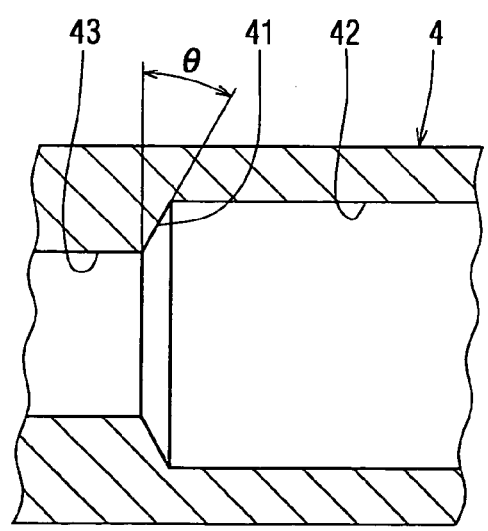
FIG. 13 is a partial sectional view of a modification to the third embodiment of the liquid level detecting apparatus according to the invention.

As shown in FIG. 13, the modification consists in altering the shape of the correcting reflective surface (step) 41 of the fuel liquid level detecting apparatus 1C. In the modification, the correcting reflective surface (step) 41 is formed in the shape of a conical surface the axis of which is identical to that of the transmission route A.

In this case, an angle θ shown in FIG. 13 is set so that a reflected wave reflected by the correcting reflective surface 41 may directly enter the ultrasonic sensor 3, whereby the same effects as in the fuel liquid level detecting apparatus 1C are attained.

In the fuel liquid level detecting apparatus 1C, the guide pipes 4 and 5 are formed as separate members, which are assembled together, but they may well be unitarily formed.

Besides, the guide pipe 5 in the fuel liquid level detecting apparatus 1C may well be omitted.

Besides, in the fuel liquid level detecting apparatus 1C, the reflective surface 44 is shaped in a flat surface, but it may well be shaped in a concave surface which is concave facing both the ultrasonic generation surface 31 and the liquid level 81.

(Fourth Embodiment)

Figure 14:
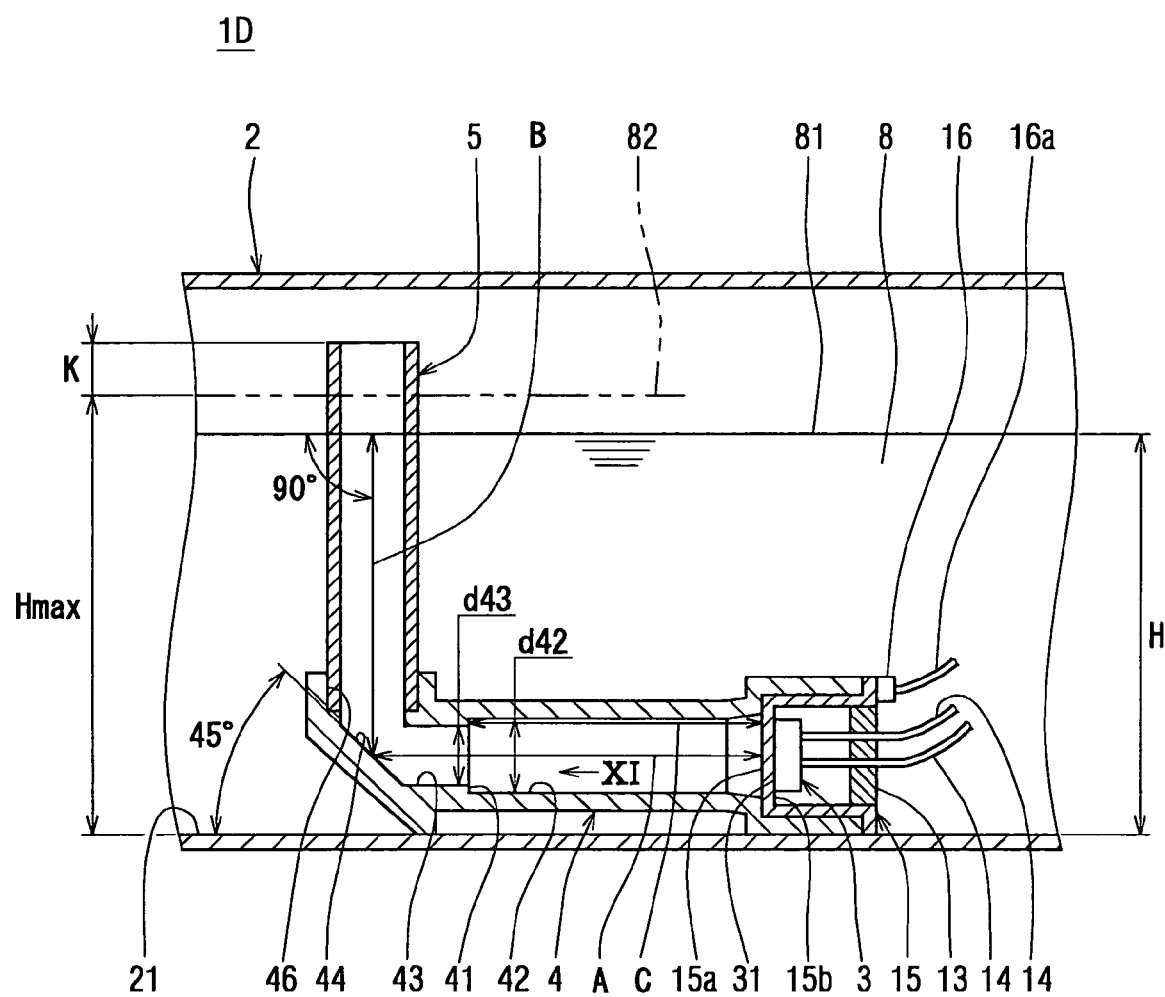
FIG. 14 is a partial sectional view of the fourth embodiment of the liquid level detecting apparatus according to the invention.
Figure 15:
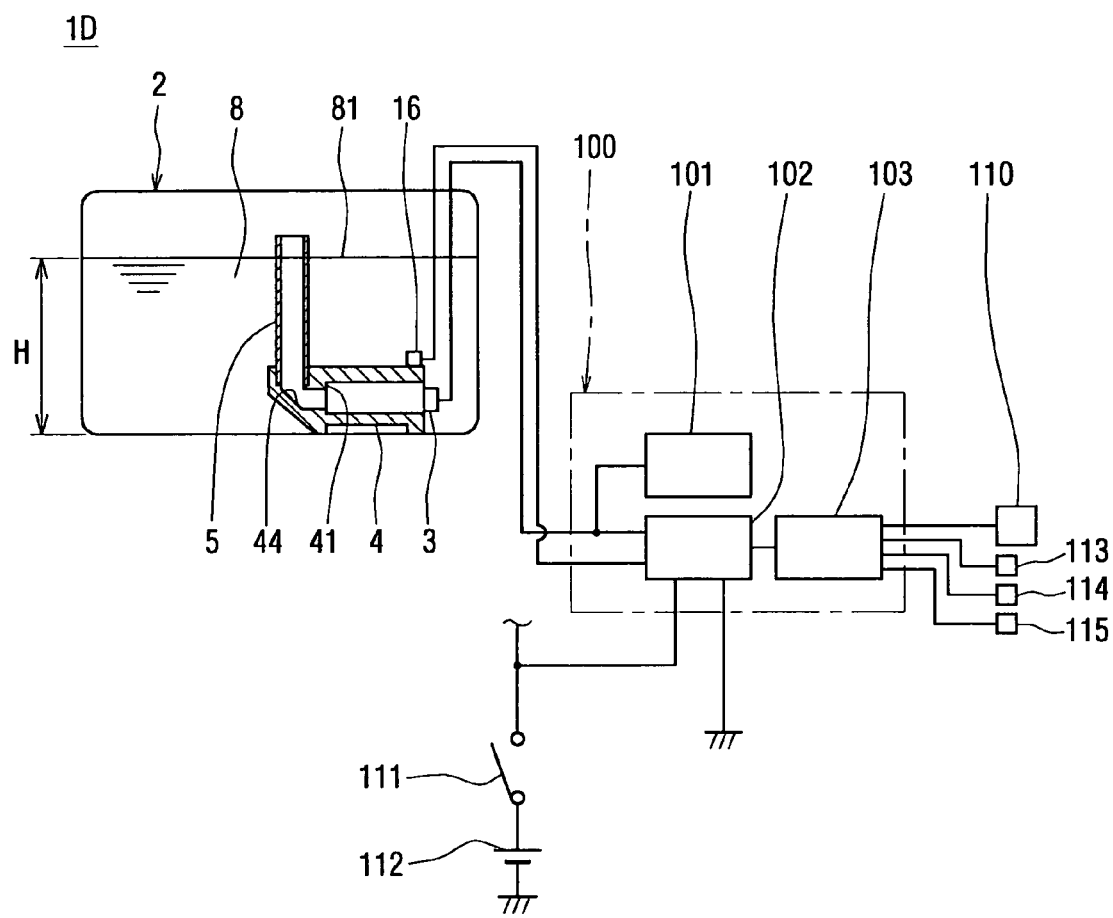
FIG. 15 is a schematic diagram showing an electric circuit arrangement in the fourth embodiment of the liquid level detecting apparatus according to the invention.

As shown in FIGS. 14 and 15, according to a fuel liquid level detecting apparatus 1D in the fourth embodiment, a temperature sensor (temperature detection means) 16 for detecting the temperature of a fuel 8 is attached to the bracket 15 of the fuel liquid level detecting apparatus 1C in the third embodiment. Besides, in a control circuit 100, an arithmetic circuit 102 decides whether or not the fuel 8 with which a fuel tank 2 has been replenished is of a predetermined kind. Light emitting diodes 113, 114 and a beeper 115 are connected to drive means 103 as report means for notifying the results of the decisions. The other constituents of the fuel liquid level detecting apparatus 1D are constructed similarly to the corresponding constituents of the fuel liquid level detecting apparatus 1C, respectively.

The temperature sensor 16 is constructed of a thermistor, and is attached to the bracket 15. This temperature sensor 16 is connected to an external electric circuit through a lead wire 16a.

The electric circuit arrangement of the fuel liquid level detecting apparatus 1D will be described with reference to FIG. 15.

The arithmetic circuit 102 calculates the position of a liquid level 81, and it also decides the kind of the fuel 8, namely, the kind of a liquid. The red LED (light emitting diode) 113, orange LED 114 and beeper 115 are connected as the report means to the drive circuit 103. In case of the decision of the arithmetic circuit 102 that the fuel 8 within the fuel tank 2 is not of the predetermined kind, the drive circuit 103 drives the red LED 113 or the orange LED 114 to turn ON, and it sounds the beeper 115, thereby to give warning to the driver of an automobile.

Next, the operation of detecting the fuel liquid level in the fuel liquid level detecting apparatus 1D will be described.

An ultrasonic sensor 3 is impressed with a pulse-shaped voltage signal by a pulse generation circuit 101, and it generates a pulse-shaped ultrasonic wave into the fuel 8 within the fuel tank 2. The ultrasonic generation surface 31 of the ultrasonic sensor 3 vibrates, the vibration of the ultrasonic generation surface 31 is conveyed to the bottom 15b of the bracket 15, and an ultrasonic wave is further generated from the outside surface 15a of the bracket 15 into the fuel 8. Part of this ultrasonic wave proceeds inside a guide pipe 4 by tracing a transmission route C shown in FIG. 14, and enters a correcting reflective surface 41. The partial ultrasonic wave is reflected there, and it enters the ultrasonic generation surface 31 of the ultrasonic sensor 3 again by tracing the transmission route C. On the other hand, part of the pulse-shaped ultrasonic wave generated from the ultrasonic sensor 3 into the fuel 8 proceeds inside the guide pipe 4 by tracing a transmission route A shown in FIG. 14 and enters a measuring reflective surface 44. The partial ultrasonic wave is reflected by the measuring reflective surface 44, and it proceeds inside a guide pipe 5 and toward the liquid level 81 by tracing a transmission route B shown in FIG. 14. Further, it is reflected by the liquid level 81, and it enters the ultrasonic sensor 3 along the same route as that of the going path, that is, via the transmission route B, measuring reflective surface 44 and transmission route A again.

Thus, when the ultrasonic sensor 3 is driven by the pulse generation circuit 101 to generate the single ultrasonic pulse, it receives the two reflected pulses; the reflected pulse from the correcting reflective surface 41 and the reflected pulse from the liquid level 81, in correspondence with the single-pulse generation as stated above. As seen from FIG. 14, a transmission route length from the ultrasonic sensor 3 to the correcting reflective surface 41 is less than a transmission route length from the ultrasonic sensor 3 to the liquid level 81. Therefore, the ultrasonic sensor 3 first receives the reflected pulse from the correcting reflective surface 41 and subsequently receives the reflected pulse from the liquid level 81. When the ultrasonic sensor 3 receives the respective reflected pulses, it generates voltage signals, which are inputted to the arithmetic circuit 102.

The arithmetic circuit 102 calculates time periods which are expended since the issue of the pulse-shaped voltage signal by the pulse generation circuit 101, till the detections of the two reflected pulses stated above, that is, a first round-trip time t1 being a time period in which the ultrasonic wave goes and comes back between the ultrasonic sensor 3 and the correcting reflective surface 41, and a second round-trip time t2 being a time period in which the ultrasonic wave goes and comes back between the ultrasonic sensor 3 and the liquid level 81 via the measuring reflective surface 44, respectively.

Here, the correcting reflective surface 41 is provided at a predetermined position relative to the ultrasonic sensor 3. That is, the distance between the correcting reflective surface 41 and the ultrasonic sensor 3 is known. Accordingly, the arithmetic circuit 102 calculates a measured propagation velocity V1 being the propagation velocity of the ultrasonic pulse in the fuel 8, on the basis of the time period since the issue of the pulse-shaped voltage signal by the pulse generation circuit 101 till the reception of the reflected pulse from the correcting reflective surface 41, and the distance between the correcting reflective surface 41 and the ultrasonic sensor 3. Subsequently, the arithmetic circuit 102 calculates the position of the liquid level 81, namely, the height H of the liquid level 81 in FIG. 14, on the basis of the measured propagation velocity V1 being the propagation velocity of the ultrasonic pulse in the fuel 8 as thus calculated, and the second round-trip time t2 being the time period since the issue of the pulse-shaped voltage signal by the pulse generation circuit 101 till the reception of the reflected pulse from the liquid level 81. Further, the arithmetic circuit 102 calculates the reserve of the fuel 8 within the fuel tank 2, on the basis of the prestored shape of the fuel tank 2.

Meanwhile, the propagation velocity of an ultrasonic pulse in a liquid changes as the temperature of the liquid changes. In this regard, in the fuel liquid level detecting apparatus 1D, the correcting reflective surface 41 is provided to calculate the first round-trip time t1, whereby the ultrasonic-pulse propagation velocity in the fuel 8 at each point of time can be accurately calculated. In the fuel liquid level detecting apparatus 1D, accordingly, the data of the temperature of the fuel 8 as detected by the temperature sensor 16 is not employed in the liquid-level detecting operation.

The drive circuit 103 outputs a signal for causing a display unit 110 to display the height H of the liquid level 81 or the reserve of the fuel 8 as calculated by the arithmetic circuit 102, for example, a drive signal for turning a needle shaft (not shown) up to an angle which corresponds to the height H of the liquid level 81 or the reserve of the fuel 8. Thus, the height H of the liquid level 81 in the fuel tank 2 or the reserve of the fuel 8 is displayed by the display unit 110.

Next, there will be described the operation of deciding the kind of the liquid by the control circuit 100 as forms the characterizing feature of the fuel liquid level detecting apparatus 1D.

Here in the fuel liquid level detecting apparatus 1D, the fuel 8 is assumed to be gasoline. Then, in case of feeding oil into the fuel tank 2 at a gasoline station, the regular fuel 8 is the gasoline, and a fuel which might be erroneously fed is light oil.

In the fuel liquid level detecting apparatus 1D, accordingly, the liquid decision circuit 102 of the control circuit 100 decides whether the liquid in the fuel tank 2 is the gasoline, the light oil, or water.

Figure 16:
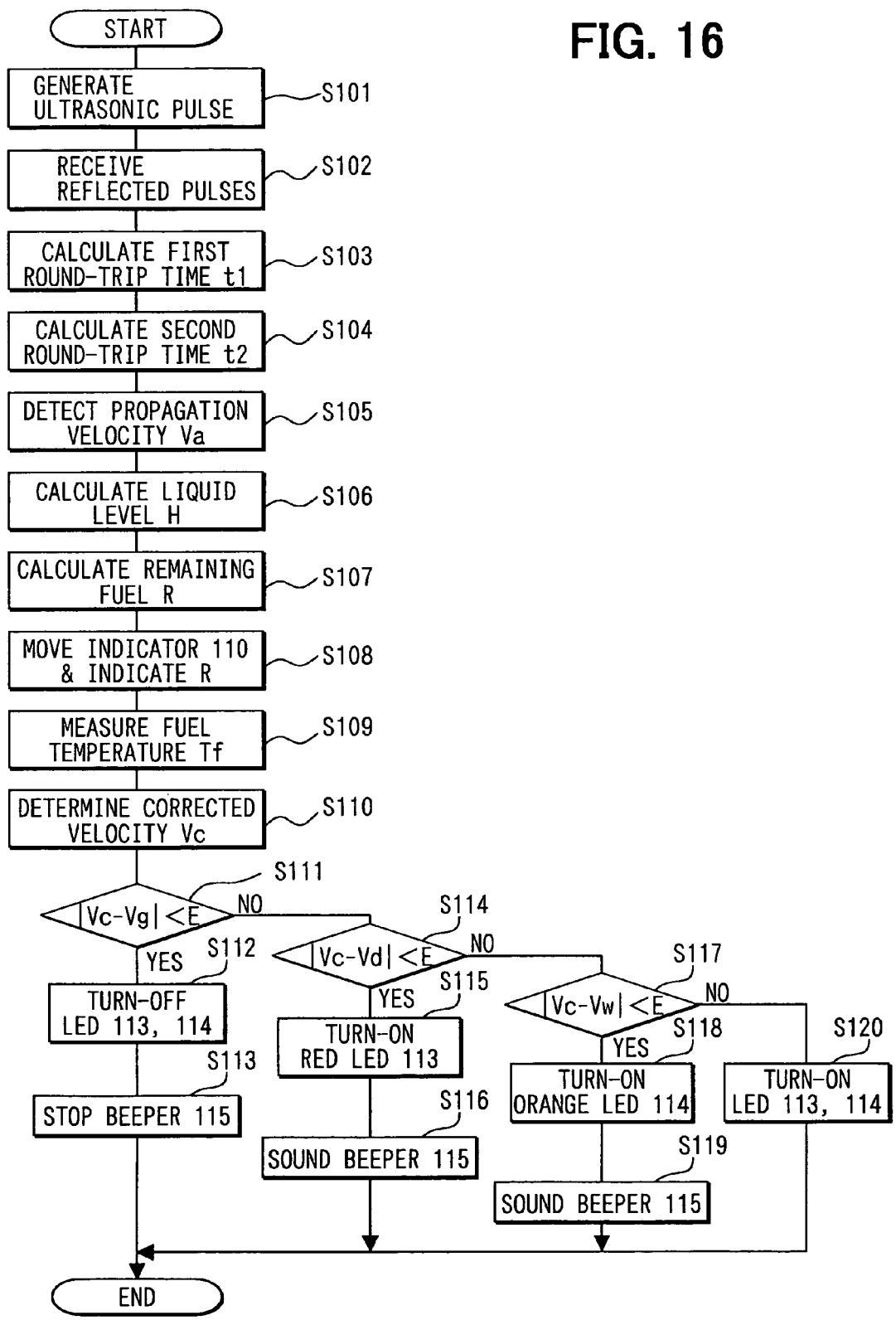
FIG. 16 is a flow chart showing a process based on a control circuit, in the fourth embodiment of the liquid level detecting apparatus according to the invention.

FIG. 16 is a flow chart for explaining the operation of the control circuit 100 in the fuel liquid level detecting apparatus 1D.

At steps S101 through S108 in FIG. 16, the position of the liquid level 81 is detected, a remaining fuel quantity R in the fuel tank 2 is calculated, and the remaining fuel quantity R is displayed on the display unit 110. Subsequently, at steps S109 through S120 in FIG. 16, the kind of the liquid in the fuel tank 2 is decided.

In the first place, there will be described the operations of the detection of the liquid level 81—the display of the remaining fuel quantity R as based on the control circuit 100 of the fuel liquid level detecting apparatus 1D.

When an ignition switch 111 has been closed by the driver, the control circuit 100 starts operating.

First, at the step S101, the pulse generation circuit 101 is driven to generate an ultrasonic pulse from the ultrasonic sensor 3.

Subsequently, at the step S102, a reflected wave from the correcting reflective surface 41, and a reflected wave from the liquid level 81 via the measuring reflective surface 44 are respectively detected by the arithmetic circuit 102.

Subsequently, at the step S103, the first round-trip time t1 being the time period in which the ultrasonic pulse goes and comes back between the ultrasonic sensor 3 and the correcting reflective surface 41 is calculated by the arithmetic circuit 102.

Subsequently, at the step S104, the second round-trip time t2 being the time period in which the ultrasonic pulse goes and comes back between the ultrasonic sensor 3 and the liquid level 81 via the measuring reflective surface 44 is calculated by the arithmetic circuit 102.

Subsequently, at the step S105, a measured propagation velocity Va which is the propagation velocity of the ultrasonic pulse in the fuel 8 at this point of time is calculated on the basis of the first round-trip time t1.

Subsequently, at the step S106, the position H of the liquid level 81 is calculated on the basis of the measured propagation velocity Va.

Subsequently, at the step S107, the remaining fuel quantity R which is a fuel reserve in the fuel tank 2 is calculated on the basis of the position H of the liquid level 81.

Subsequently, at the step S108, the display unit 110 is driven by the drive circuit 103 so as to display the remaining fuel quantity R thereon.

The above is the liquid-level-81 detection operation—the remaining-fuel-quantity-R display operation by the control circuit 100 of the fuel liquid level detecting apparatus 1D.

In the second place, there will be described the liquid-kind decision operation by the control circuit 100 as forms the characterizing feature of the fuel liquid level detecting apparatus 1D.

First, a fuel temperature Tf is detected at the step S109.

Subsequently, at the step S110, the measured propagation velocity Va is corrected on the basis of the fuel temperature Tf by the arithmetic circuit 102, whereby a corrected measured propagation velocity Vc is calculated. Here in the fuel liquid level detecting apparatus 1D, the corrected measured propagation velocity Vc is calculated as a value at 20° C.

Subsequently, at the step S111, the difference between the corrected measured propagation velocity Vc and a reference propagation velocity Vg being reference propagation velocity data is calculated in the arithmetic circuit 102. The reference propagation velocity Vg is the ultrasonic propagation velocity of the fuel 8, namely, gasoline at 200C, and it is prestored in a storage unit (not shown) within the arithmetic circuit 102.

On this occasion, if the difference between the corrected measured propagation velocity Vc and the reference propagation velocity Vg lies within an error range E, it is decided that the corrected measured propagation velocity Vc is substantially equal to the reference propagation velocity Vg, in other words, that the fuel 8 is the gasoline.

It is accordingly unnecessary to actuate any of the red LED 113, orange LED 114 and beeper 115 which are the report means. Therefore, both the LEDs 113 and 114 are turned OFF at the step S112, and the beeper 115 is stopped at the step S113.

If, at the step S111, the difference between the corrected measured propagation velocity Vc and the reference propagation velocity Vg exceeds the error range E, it is judged that the fuel 8 is any liquid other than the gasoline. Then, the control circuit 100 shifts to an operation for specifying the kind of the liquid as will be explained below.

Subsequently, at the step S114, the difference between the corrected measured propagation velocity Vc and a reference propagation velocity Vd being reference propagation velocity data is calculated in the arithmetic circuit 102. The reference propagation velocity Vd is the ultrasonic propagation velocity of light oil at 20° C., and it is prestored in the storage unit (not shown) within the arithmetic circuit 102.

On this occasion, if the difference between the corrected measured propagation velocity Vc and the reference propagation velocity Vd lies within the error range E, it is decided that the corrected measured propagation velocity Vc is substantially equal to the reference propagation velocity Vd, in other words, that the fuel 8 is the light oil.

Accordingly, the arithmetic circuit 102 renders the decision that the fuel 8 is the light oil, and it commands the drive circuit 103 to drive the red LED 113 and the beeper 115 which are the report means.

When a gasoline engine has been fuelled with the light oil, it becomes incapable of starting. It is therefore necessary to promptly empty the fuel tank 2 and then supply the gasoline anew, and to take such a measure as cleaning a fuel passage from the fuel tank 2 to the engine and then filling up the passage with the gasoline.

Consequently, the red LED 113 is turned ON at the step S115, and also the beeper 115 is sounded at the step S116, whereby the driver is reliably prompted to take the necessary measures.

If, at the step S114, the difference between the corrected measured propagation velocity Vc and the reference propagation velocity Vd is greater the error range E, it is judged that the fuel 8 is any liquid other than the gasoline and the light oil, and the step S117 is executed.

Here at the step S117, the difference between the corrected measured propagation velocity Vc and a reference propagation velocity Vw being reference propagation velocity data is calculated in the arithmetic circuit 102. The reference propagation velocity Vw is the ultrasonic propagation velocity of water at 20° C., and it is prestored in the storage unit (not shown) within the arithmetic circuit 102.

On this occasion, if the difference between the corrected measured propagation velocity Vc and the reference propagation velocity Vw is less than the error range E, it is decided that the corrected measured propagation velocity Vc is substantially equal to the reference propagation velocity Vw, in other words, that the liquid 8 is the water.

Accordingly, the arithmetic circuit 102 renders the decision that the liquid 8 is the water, and it commands the drive circuit 103 to drive the orange LED 114 and the beeper 115 which are the report means.

Consequently, the orange LED 114 is turned ON at the step S118, and also the beeper 115 is sounded at the step S119, whereby the driver is reliably prompted to take necessary measures.

Here, it is usually impossible that the water be injected into the fuel tank 2 in a fueling job. The stay of the water in the fuel tank 2 is ascribable to the fact that waterdrops in a slight amount have intruded through an oil feeding port in case of fueling on a rainy day or the like, or that water vapor in the air within the fuel tank 2 has formed dewdrops due to a temperature fall and has mixed into the fuel 8. Besides, since the specific weight of the water is greater than that of the fuel 8, namely, the gasoline or the light oil, the water stays in the bottom of the fuel tank 2. In other words, the water stays at the peripheral part of the fuel liquid level detecting apparatus 1D, for example, within the guide pipe 4.

Thus, when the quantity of the water staying in the fuel tank 2 has reached a certain quantity, the fuel liquid level detecting apparatus 1D can reliably detect the situation as stated above.

If, at the step S117, the difference between the corrected measured propagation velocity Vc and the reference propagation velocity Vw is greater than the error range E, it is judged that the fuel 8 is any liquid other than the gasoline, the light oil and the water.

In this case, the driver needs to promptly check what is the liquid within the fuel tank 2.

Therefore, the arithmetic circuit 102 issues a command to the drive circuit 103 so as to simultaneously turn ON the red LED 113 and the orange LED 114 at the step S120.

In the fuel liquid level detecting apparatus 1D described above, the measured propagation velocity Va being the ultrasonic propagation velocity in the fuel 8 as calculated in the course of the liquid level detecting operation is corrected to the value at 20° C., on the basis of the fuel temperature Tf, whereby the corrected measured propagation velocity Vc is calculated. On the other hand, in the control circuit 100, the ultrasonic propagation velocities in the several liquids, for example, the gasoline, light oil and water at 20° C. are prestored as the reference propagation velocity data. Besides, the corrected measured propagation velocity Vc is compared with the respective reference propagation velocities Vg, Vd and Vw, whereby the kind of the liquid in the fuel tank 2 is distinguishable. That is, it is decided that the liquid whose reference propagation velocity is equal to or nearest to the corrected measured propagation velocity Vc is the liquid in the tank.

Thus, the kind of the liquid in the fuel tank 2 can be discriminated easily and accurately. It is therefore possible to realize the fuel liquid level detecting apparatus 1D which can prevent the occurrence of any drawback ascribable to the actuation of the automobile in the state where the liquid of the kind different from the predetermined liquid or the gasoline, has been injected into the fuel tank 2 or has mixed thereinto.

Here in the fuel liquid level detecting apparatus 1D, the comparison of the propagation velocities of the ultrasonic wave is made using the data at 20° C. That is, the comparison is made under the same temperature condition. Thus, the liquid can be discriminated at a high accuracy.

By the way, in such a case where the range of the changes of the fuel temperature within the fuel tank 2 is limited, the temperature sensor 16 may well be omitted so as to discriminate the liquid by using the measured propagation velocity Va, not the corrected measured propagation velocity Vc.

(Fifth Embodiment)

Figure 17:
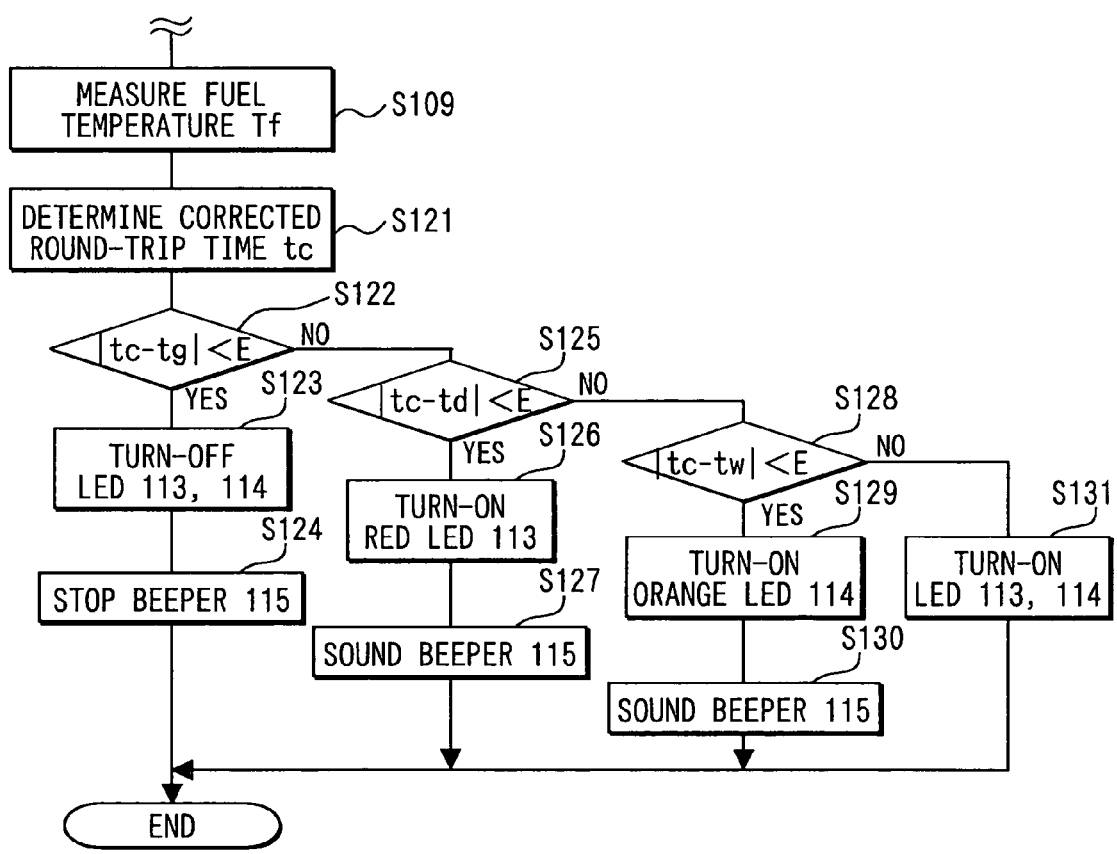
FIG. 17 is a flow chart showing a process based on a control circuit, in the fifth embodiment of the liquid level detecting apparatus according to the invention.

Shown in FIG. 17 is a flow chart for explaining the operation of a control circuit 100 in a fuel liquid level detecting apparatus 1D in the fifth embodiment. By the way, in FIG. 17, parts relevant to a liquid level detecting operation, namely, steps S101–S108 are omitted because they are the same as in the fourth embodiment.

In the fuel liquid level detecting apparatus 1D of the fourth embodiment, the discrimination of the liquid kind is done on the basis of the ultrasonic propagation velocities in the liquid 8. In contrast, in the fuel liquid level detecting apparatus 1D of the fifth embodiment, the liquid discrimination is implemented on the basis of a first round-trip time t1 being a time period in which an ultrasonic wave goes and comes back between an ultrasonic sensor 3 and a correcting reflective surface 41.

Hereinbelow, the same parts as in the fuel liquid level detecting apparatus 1D of the fourth embodiment shall be omitted from description, and only parts peculiar to the fuel liquid level detecting apparatus 1D of the fifth embodiment will be described.

As shown in FIG. 17, at a step S121, the first round-trip time t1 is corrected on the basis of a fuel temperature Tf detected at a step S109, thereby to calculate a corrected round-trip time tc. Here in the fuel liquid level detecting apparatus 1D of the fifth embodiment, the corrected round-trip time tc is calculated as a value at 20° C.

Subsequently, at a step S122, the difference between the corrected round-trip time tc and a reference round-trip time tg being reference round-trip time data is calculated in an arithmetic circuit 102. The reference round-trip time tg is a first round-trip time at 20° C. in the case where the fuel 8 is gasoline, and it is prestored in a storage unit (not shown) within the arithmetic circuit 102.

On this occasion, if the difference between the corrected round-trip time tc and the reference round-trip time tg is less than an error range F, it is decided that the corrected round-trip time tc is substantially equal to the reference round-trip time tg, in other words, that the fuel 8 is the gasoline.

It is accordingly unnecessary to actuate any of a red LED 113, an orange LED 114 and a beeper 115 which are report means. Therefore, both the LEDs 113 and 114 are turned OFF at a step S123, and the beeper 115 is stopped at a step S124.

If, at the step S122, the difference between the corrected round-trip time tc and the reference round-trip time tg is greater than the error range F, it is judged that the fuel 8 is any liquid other than the gasoline. Then, the control circuit 100 shifts to an operation for specifying the kind of the liquid as will be explained below.

Subsequently, at a step S125, the difference between the corrected round-trip time tc and a reference round-trip time td being reference round-trip time data is calculated in the arithmetic circuit 102. The reference round-trip time td is a first round-trip time at 20° C. in the case where the fuel 8 is light oil, and it is prestored in the storage unit (not shown) within the arithmetic circuit 102.

On this occasion, if the difference between the corrected round-trip time tc and the reference round-trip time td is less than the error range F, it is decided that the corrected round-trip time tc is substantially equal to the reference round-trip time td, in other words, that the fuel. 8 is the light oil.

Thus, the arithmetic circuit 102 renders the decision that the fuel 8 is the light oil, and it commands a drive circuit 103 to drive the red LED 113 and beeper 115 which are the report means. Consequently, the red LED 113 is turned ON at a step S126, and also the beeper 115 is sounded at a step S127, whereby the driver of an automobile can be reliably prompted to take necessary measures.

If, at the step S125, the difference between the corrected round-trip time tc and the reference round-trip time td is greater than the error range F, it is judged that the fuel 8 is any liquid other than the gasoline and the light oil, followed by a step S128.

Here at the step S128, the difference between the corrected round-trip time tc and a reference round-trip time tw being reference round-trip time data is calculated in the arithmetic circuit 102. The reference round-trip time tw is a first round-trip time at 20° C. in the case of water, and it is prestored in the storage unit (not shown) within the arithmetic circuit 102.

On this occasion, if the difference between the corrected round-trip time tc and the reference round-trip time tw is less than the error range F, it is decided that the corrected round-trip time tc is substantially equal to the reference round-trip time td, in other words, that the liquid 8 is the water.

Thus, the arithmetic circuit 102 renders the decision that the liquid 8 is the water, and it commands the drive circuit 103 to drive the orange LED 114 and beeper 115 which are the report means. Consequently, the orange LED 114 is turned ON at a step S129, and also the beeper 115 is sounded at a step S130, whereby the driver can be reliably prompted to take necessary measures.

If, at the step S128, the difference between the corrected round-trip time tc and the reference round-trip time tw is greater than the error range F, it is judged that the fuel 8 is any liquid other than the gasoline, the light oil and the water.

In this case, the driver needs to promptly check what is the liquid within the fuel tank 2.

Therefore, the arithmetic circuit 102 issues a command to the drive circuit 103 so as to simultaneously turn ON the red LED 113 and the orange LED 114 at a step S131.

As described above, also the fuel liquid level detecting apparatus 1D of the fifth embodiment can discriminate the kind of the liquid in the fuel tank 2 easily and accurately. Therefore, it is reliably found that the liquid of the kind different from the predetermined liquid or the gasoline has been injected into the fuel tank 2.

Incidentally, each of the fuel liquid level detecting apparatuses 1D in the fourth and fifth embodiments is constructed so that the liquid kind discriminating operation may be performed integrally with and continuously to the liquid level position detecting operation. However, the liquid level position detecting operation need not always be performed, but it may well be executed at limited timings in accordance with predetermined rules. By way of example, although no illustration is made, the liquid level position detecting operation may well be executed one time—several times immediately after the ignition switch 111 has been closed by the driver. Alternatively, the liquid level position detecting operation may well be executed one time—several times immediately after the ignition switch 111 has been closed by the driver subsequently to the replenishment of the fuel tank 2 with the fuel 8. In this case, the replenishment of the fuel tank 2 with the fuel 8 can be detected by, for example, disposing a sensor which detects that the lid of the fuel feeding port of the automobile has been opened and shut.

Besides, in each of the fuel liquid level detecting apparatuses 1D according to the first and second embodiments of the invention as described before, the red LED 113 and the orange LED 114 are employed as the report means. However, the colors of light emissions need not be restricted to the exemplary ones, but other colors may well be adopted. Also, a display unit (not shown) as report means may well be formed by performing a translucent coloring process in a character panel (not shown) on which the display unit 110, etc. are to be installed. In that case, the red LED 113 and orange LED 114 may well be substituted by white LEDs, electric bulbs or the likes. Alternatively, the behavior of the fuel, namely, the kind of the fuel may, of course, be delivered as a message by a liquid crystal display.

Besides, in each of the fuel liquid level detecting apparatuses 1D in the fourth and fifth embodiments, the beeper 115 is employed as the report means. However, the beeper 115 need not be restricted to a beeper of so-called "electromagnetic type", but several warning sounds may well be synthesized by an electronic circuit so as to be emitted by a loudspeaker or the like.

(Sixth Embodiment)

Figure 18:
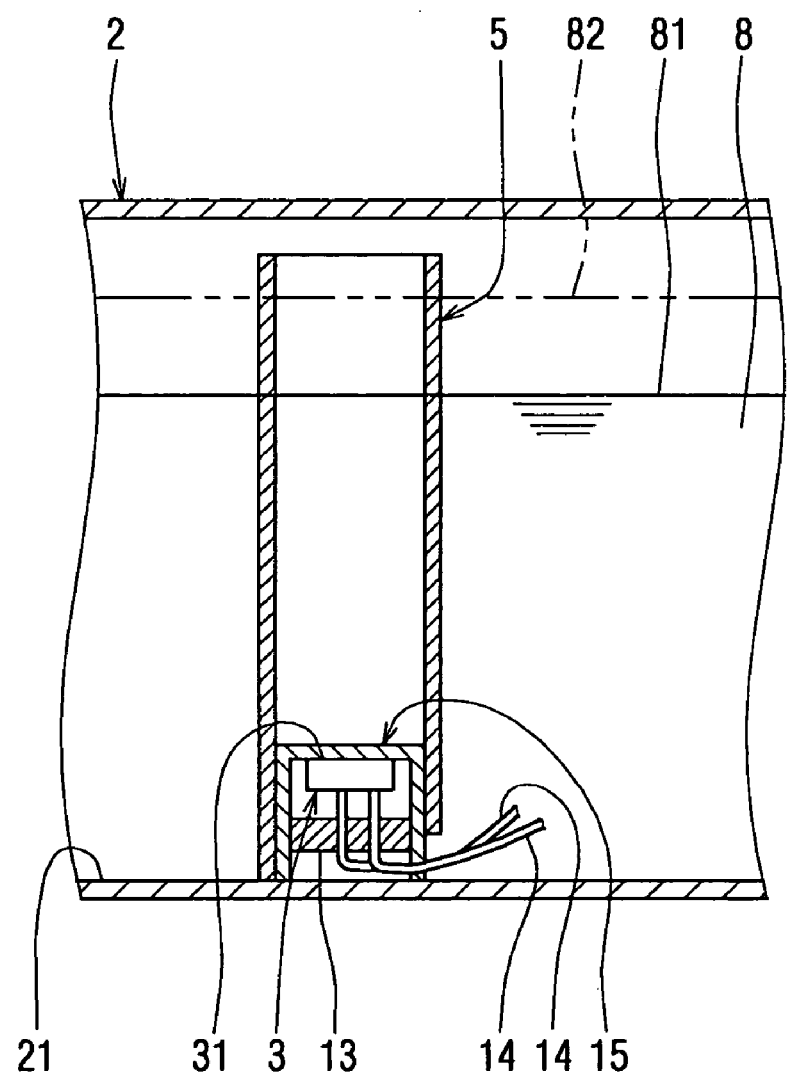
FIG. 18 is a partial sectional view of the sixth embodiment of the liquid level detecting apparatus according to the invention.

Shown in FIG. 18 is a partial sectional view of a fuel tank 2 which is furnished with a fuel liquid level detecting apparatus 1E in the sixth embodiment. By the way, in FIG. 18, the same reference numerals are respectively assigned to the same parts as in FIG. 14.

In the fuel liquid level detecting apparatus 1E of the sixth embodiment, the guide pipe 4 in the fuel liquid level detecting apparatus 1D of the fourth embodiment is done away with, and the ultrasonic sensor 3 is fixed at the lower end part of the guide pipe 5. Besides, the ultrasonic sensor 3 is attached in an attitude in which it can generate an ultrasonic wave directly toward a liquid level 81 as shown in FIG. 18.

In the fuel liquid level detecting apparatus 1E, the ultrasonic sensor 3 generates the ultrasonic wave therefrom and receives a reflected wave from the liquid level 81. Thus, the detecting apparatus 1E calculates a time period in which the ultrasonic wave makes a round trip between the ultrasonic sensor 3 and the liquid level 81, and it detects the liquid level 81 on the basis of the calculated time period.

Besides, in the fuel liquid level detecting apparatus 1E, a liquid kind discriminating operation is executed only immediately after the fuel tank 2 has been fed with a fuel 8.

In the job of feeding the fuel 8 for an automobile, the fuel tank 2 is generally brought into a full tank state. Besides, the position of the highest liquid level 82 as is a liquid level position in the full tank state is substantially identical every fuel feeding job, and the distance between the ultrasonic generation surface 31 of the ultrasonic sensor 3 and the highest liquid level 82 is a known value.

Accordingly, the kind of any liquid fed into the fuel tank 2 can be reliably discriminated in such a way that a measured round-trip time, which is the round-trip time period of the ultrasonic wave between the ultrasonic generation surface 31 of the ultrasonic sensor 3 and the highest liquid level 82 as has been measured immediately after the fuel feeding, is compared with reference round-trip times, which are the round-trip time periods between the ultrasonic generation surface 31 and the highest liquid level 82 within various liquids (fuels) as are prestored in a control circuit 100.

Usually, during the fuel feeding job, an ignition switch 111 is kept turned-OFF for the sake of safety. Besides, the completion of the fuel feeding into the fuel tank 2 can be sensed by such a method as detecting the opening and shutting of the lid of an oil feeding port, or detecting the attachment and detachment of an oil feeding nozzle to and from the oil feeding port.

Here in the fuel liquid level detecting apparatus 1E of the sixth embodiment, the liquid kind discriminating operation is implemented at the point of time at which the ignition switch 111 has been first turned ON after the detection of the completion of the fuel feeding into the fuel tank 2.

Thus, also in the fuel liquid level detecting apparatus 1E, the kind of the liquid in the fuel tank 2 can be discriminated easily and accurately.

Incidentally, a probability at which any liquid other than a regular fuel mixes into the fuel tank 2 of the automobile is the maximum in the fuel feeding job, so that even the liquid kind discriminating operation in the fuel liquid level detecting apparatus 1E is satisfactory in practical use.

Besides, it is needless to say that the liquid behavior discriminating apparatus of the invention is also applicable to a liquid level detecting apparatus which does not include a measuring reflective member or a calibrating reflective member as in each of the fuel liquid level detecting apparatuses according to the fourth and fifth embodiments, and which generates an ultrasonic wave from an ultrasonic generation sensor into a liquid and measures a time period expended since the generation of the ultrasonic wave by the ultrasonic generation sensor, till the reception of a reflected wave reflected by the liquid level of the liquid, thereby to detect the liquid level position of the liquid (refer, for example, to JP2001-208595A).

(Seventh Embodiment)

Figure 19:
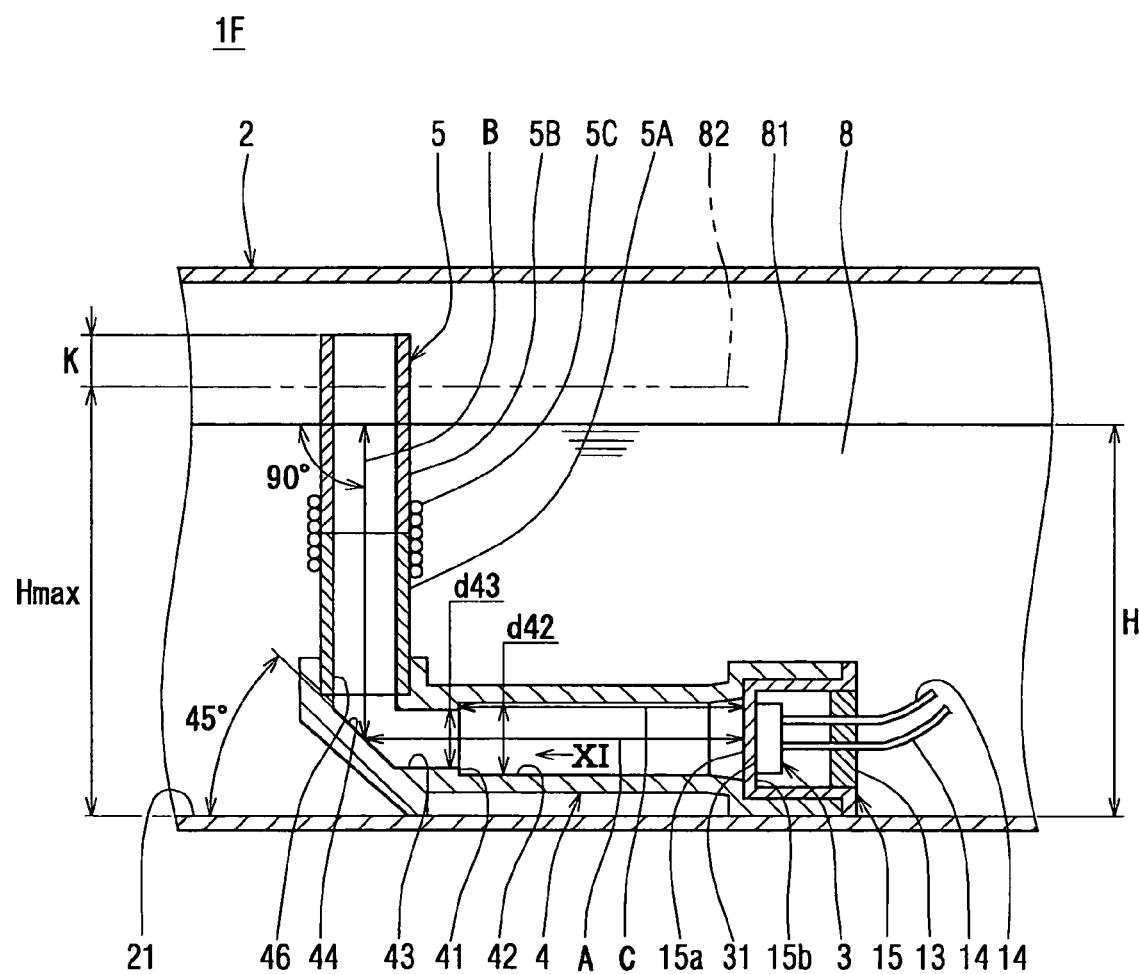
FIG. 19 is a partial sectional view of the seventh embodiment of the liquid level detecting apparatus according to the invention.
Figure 20:
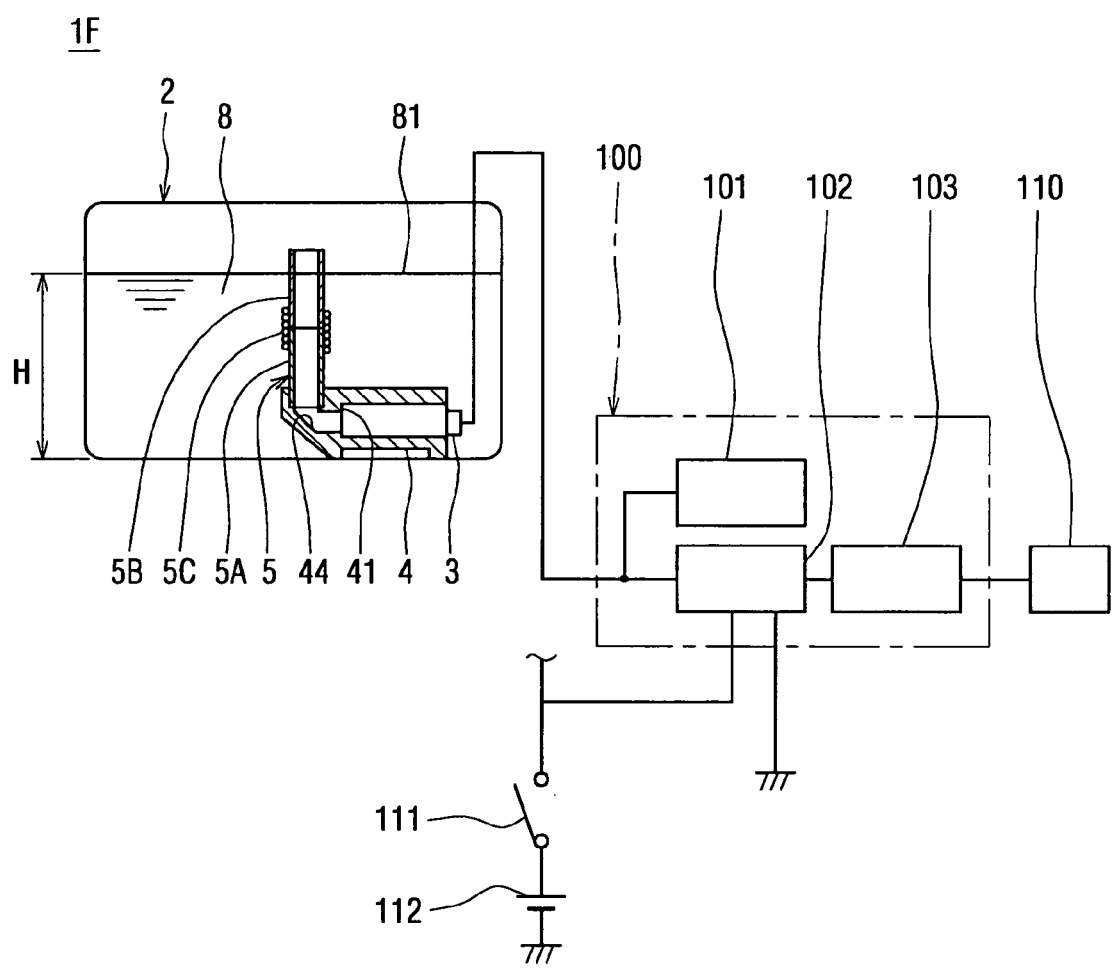
FIG. 20 is a schematic diagram showing an electric circuit arrangement in the seventh embodiment of the liquid level detecting apparatus according to the invention.

As shown in FIG. 19, according to a fuel liquid level detecting apparatus 1F in the seventh embodiment, the guide pipe 5 of the fuel liquid level detecting apparatus 1C in the third embodiment is constructed in such a way that a lower pipe 5A and an upper pipe 5B are coupled by a spring (elastic member) 5C. The other constituents of the fuel liquid level detecting apparatus 1F are constructed similarly to the corresponding constituents of the fuel liquid level detecting apparatus 1C, respectively.

Each of the lower pipe 5A and upper pipe 5B is formed of a circular tube which is made from stainless steel. The outside dimension and inside diameter dimension of the lower pipe 5A are respectively equal to those of the upper pipe 5B. The spring 5C is a close-coiled spring which is formed of a spring steel wire.

The elastic coefficient of the spring 5C is set to be much smaller than that of the lower pipe 5A as well as the upper pipe 5B. Besides, the inside diameter dimension of the spring 5C per se is set to be slightly smaller than the outside dimension of the lower pipe 5A as well as the upper pipe 5B. Thus, in a state where the lower pipe 5A and the upper pipe 5B are butted against each other, the spring 5C is snugly fitted on these pipes 5A and 5B so as to cover the joint part between both these pipes, whereby the lower pipe 5A and the upper pipe 5B are connected by the restoring force of the spring 5C.

Usually, a fuel liquid level detecting apparatus is attached into a fuel tank 2 after the apparatus itself has been assembled up. Besides, the job of attaching the fuel liquid level detecting apparatus into the fuel tank 2 is performed through, for example, an opening (not shown) for inserting a fuel pump (not shown) to be mounted inside the fuel tank 2, into this fuel tank 2 as in the fuel liquid level detecting apparatus 1F. The size of the opening is set to be small to the utmost within a range within which the job is possible. It is accordingly difficult to put the fuel liquid level detecting apparatus 1F into the fuel tank 2, the interior of which cannot be seen, through the opening, and to fix the detecting apparatus 1F to a predetermined position and in a predetermined attitude.

The guide pipe 5 of the fuel liquid level detecting apparatus 1F has its distal end protruded above a liquid level in a full tank condition, namely, the highest liquid level 82. That is, in a state where the fuel liquid level detecting apparatus 1F has been fixed in the fuel tank 2, the guide pipe 5 occupies substantially the full length of the fuel tank 2 in the depth direction thereof.

For this reason, in the prior-art liquid level detecting apparatus, there has been the possibility of the occurrence of the drawback that, in the job of the attachment into the fuel tank 2, the distal end of the guide pipe 5 will touch and damage the fuel tank 2.

In contrast, according to the fuel liquid level detecting apparatus 1F of the seventh embodiment, the guide pipe 5 is divided into the two elements, namely, the lower pipe 5A and the upper pipe 5B in its axial direction, namely, in the vertical direction of the fuel tank 2, and both the pipes 5A and 5B are unitarily fixed by the spring 5C.

Here, the spring constant of the spring 5C is set to be much smaller than the elastic coefficient of the lower pipe 5A as well as the upper pipe 5B. In other words, in a case where any external force has acted on the guide pipe 5, the lower pipe 5A and the upper pipe 5B are hardly deformed, and the spring 5C is deformed.

When the guide pipe 5 has touched the fuel tank 2 in the job of attaching the fuel liquid level detecting apparatus 1F to the fuel tank 2, the spring 5C is deformed, and the guide pipe 5 buckles with the spring 5C as an articulation.

Thus, the force acting on the fuel tank 2 decreases abruptly, and the fuel tank 2 can be prevented from being damaged by the guide pipe 5 of the fuel liquid level detecting apparatus 1F.

Further, when the external force acting on the guide pipe 5 has become extinct upon the completion of the attaching job of the fuel liquid level detecting apparatus 1F, the guide pipe 5 is restored into its original shape by the restoring force of the spring 5C. Consequently, the guide pipe 5 reliably plays the role of the ultrasonic transmission route between a measuring reflective surface 44 and a liquid level 81 in the fuel liquid level detecting apparatus 1F, so that the fuel liquid level detecting apparatus 1F operates normally.

In the fuel liquid level detecting apparatus 1F, the dynamical characteristics of the spring 5C which couples the lower pipe 5A and the upper pipe 5B are set, for example, so as to satisfy the following conditions: The guide pipe 5 is not deformed even when it has undergone the jolting of an automobile attributed to the travel thereof, the wave energy of the quaking liquid level, etc. In addition, when the guide pipe 5 has touched the fuel tank 2 in the job of attaching the fuel liquid level detecting apparatus 1F to the fuel tank 2, the spring 5C is deformed before the magnitude of the force acting on the fuel tank 2 by the guide pipe 5 reaches a level at which the fuel tank 2 is damaged.

(Eighth Embodiment)

Figure 21:
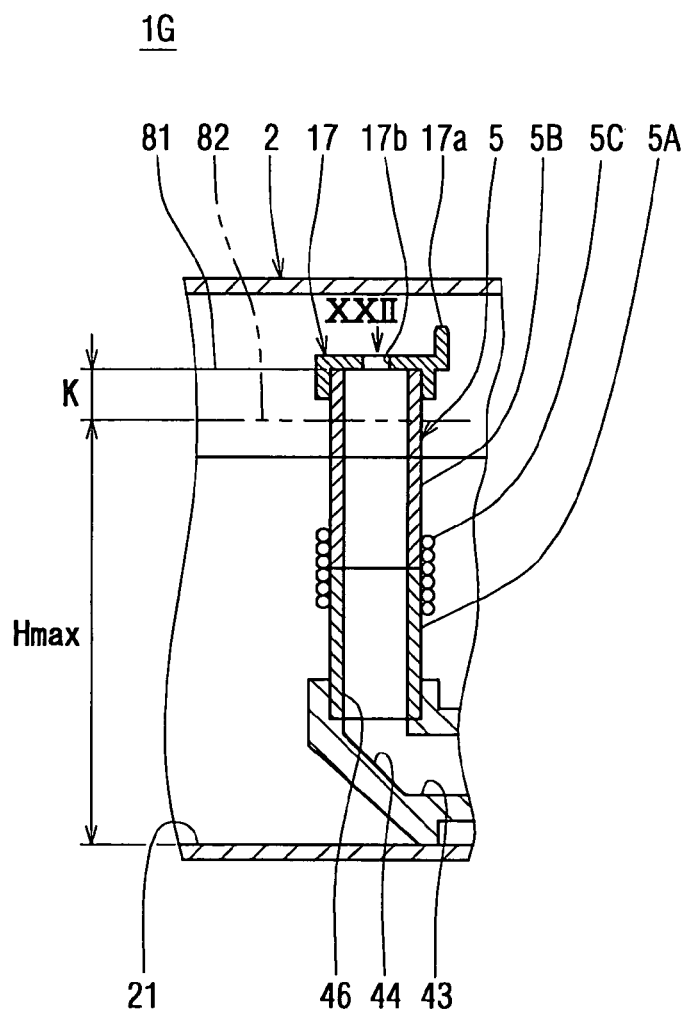
FIG. 21 is a partial sectional view of the eighth embodiment of the liquid level detecting apparatus according to the invention.

As shown in FIG. 21, a fuel liquid level detecting apparatus 1G in the eighth embodiment is such that a guard cap 17 is installed on the upper end of the guide pipe 5 of the fuel liquid level detecting apparatus 1F in the seventh embodiment. The other constituents of the fuel liquid level detecting apparatus 1G are constructed similarly to the corresponding constituents of the fuel liquid level detecting apparatus 1F (1C), respectively.

Figure 22:
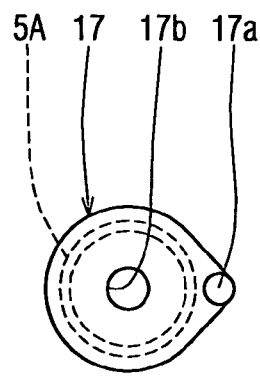
FIG. 22 is a view seen along arrow XXII in FIG. 21.

The guard cap 17 is formed from rubber or a resin material, and is snugly fitted on the upper end of the guide pipe 5 (upper pipe 5B). This guard cap 17 is formed with a protuberance 17a which extends in the axial extending direction of the guide pipe 5, that is, upwards in FIG. 21. The protuberance 17a is provided outside the contour lines of the upper pipe 5B (broken lines in FIG. 21) as shown in FIG. 22 which is a view seen along arrow XXII in FIG. 21. Further, the guard cap 17 is provided with a through hole 17b which communicates the inside of the guide pipe 5 with the interior of a fuel tank 2.

In the job of attaching the fuel liquid level detecting apparatus 1G to the fuel tank 2, when the guide pipe 5 has touched the fuel tank 2, the protuberance 17a of the guard cap 17 first comes into touch with the fuel tank 2. Here, the protuberance 17a is disposed outside the contour lines of the upper pipe 5B (broken lines in FIG. 22). Therefore, a bending moment which acts on the guide pipe 5, namely, a moment which acts so that a lower pipe 5A and the upper pipe 5B may buckle with a spring 5C as an articulation, becomes greater than in the case of the fuel liquid level detecting apparatus 1F according to the seventh embodiment.

Thus, the lower pipe 5A and the upper pipe 5B buckle with the spring 5C as the articulation, at the point of time at which a contact force is smaller. That is, owing to the touch of the distal end of the upper pipe 5B with the fuel tank 2, forces which act on the guide pipe 5 and the fuel tank 2 can be sharply decreased. Accordingly, the fuel tank 2 can be reliably prevented from being damaged by the guide pipe 5 of the fuel liquid level detecting apparatus 1G.

(Ninth Embodiment)

Figure 23:
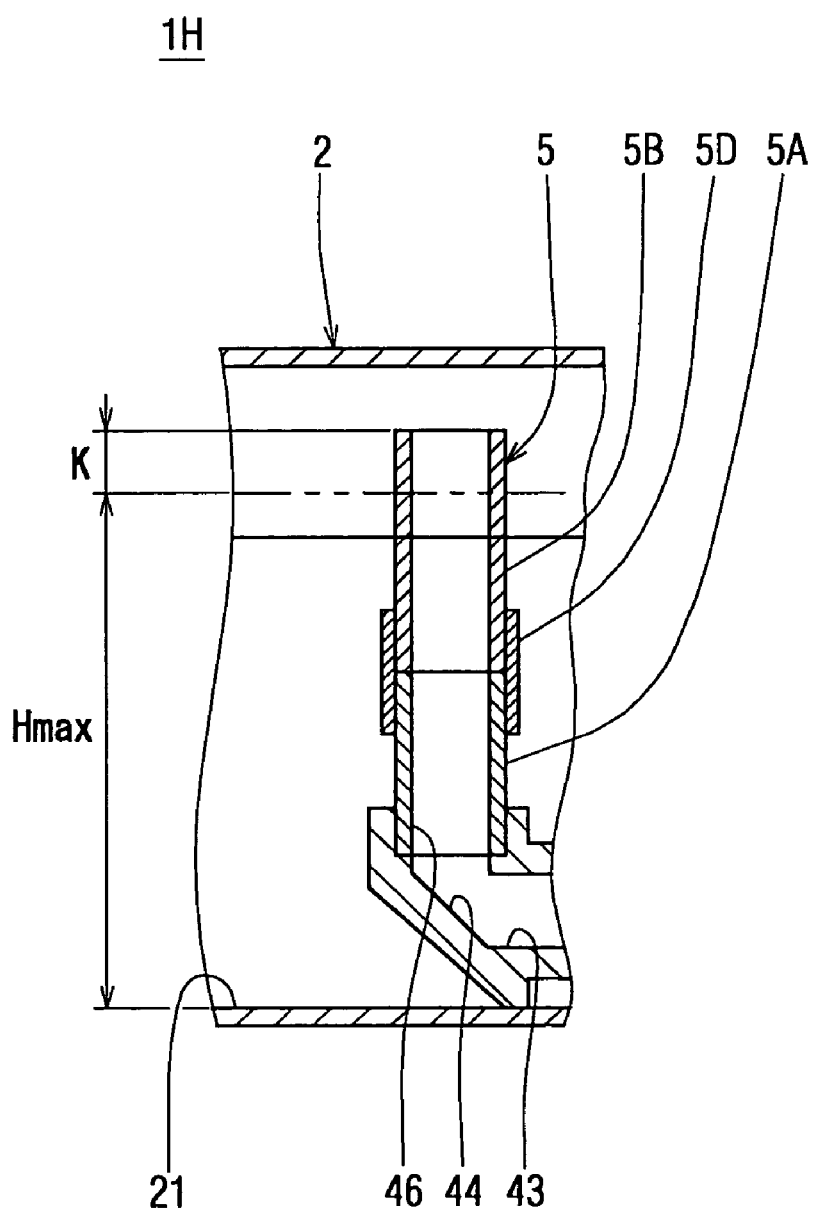
FIG. 23 is a partial sectional view of the ninth embodiment of the liquid level detecting apparatus according to the invention.

As shown in FIG. 23, a fuel liquid level detecting apparatus 1H in the ninth embodiment is such that the lower pipe 5A and upper pipe 5B of the fuel liquid level detecting apparatus 1F in the seventh embodiment are connected by a rubber pipe 5D instead of the spring 5C. The other constituents of the fuel liquid level detecting apparatus 1H are constructed similarly to the corresponding constituents of the fuel liquid level detecting apparatus 1F (1C), respectively.

Also in this case, the same effects as in the case of the fuel liquid level detecting apparatus 1F of the seventh embodiment are attained.

In the fuel liquid level detecting apparatus 1H, a material which is highly anticorrosive against a fuel 8 is chosen for the rubber pipe 5D. Besides, the dynamical characteristics of the rubber pipe 5D as the spring are set so as to fulfill the same conditions as in the case of the spring 5C in the fuel liquid level detecting apparatus 1F of the seventh embodiment.

(Tenth Embodiment)

Figure 24:
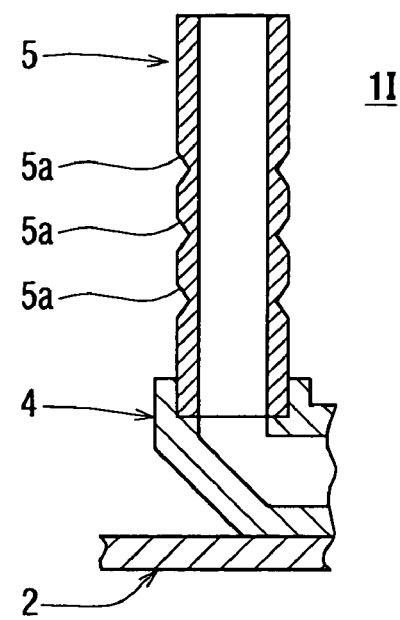
FIG. 24 is a partial sectional view of the tenth embodiment of the liquid level detecting apparatus according to the invention.

As shown in FIG. 24, a fuel liquid level detecting apparatus 11 in the tenth embodiment is such that the guide pipe 5 of the fuel liquid level detecting apparatus 1F in the seventh embodiment is constructed of a single member, and that three annular grooves 5a are formed in the outer periphery of the guide pipe 5. The other constituents of the fuel liquid level detecting apparatus 1I are constructed similarly to the corresponding constituents of the fuel liquid level detecting apparatus 1F (1C), respectively.

In the job of attaching the fuel liquid level detecting apparatus 1I to a fuel tank 2, when the guide pipe 5 has touched the fuel tank 2, bending stresses develop in the guide pipe 5. Since, however, stress concentrations occur at the parts of the annular grooves 5a, the bending stresses at these parts become much greater than the bending stresses at the other parts of the guide pipe 5. That is, the guide pipe 5 is deformed and buckled at the part of the annular groove 5a, so that the same effects as in the seventh embodiment are attained.

Incidentally, although the number of the annular grooves 5a is three in the fuel liquid level detecting apparatus 1I, a single annular groove, or two or at least four annular grooves may well be provided.

(Modification to Seventh Embodiment)

Figure 25:
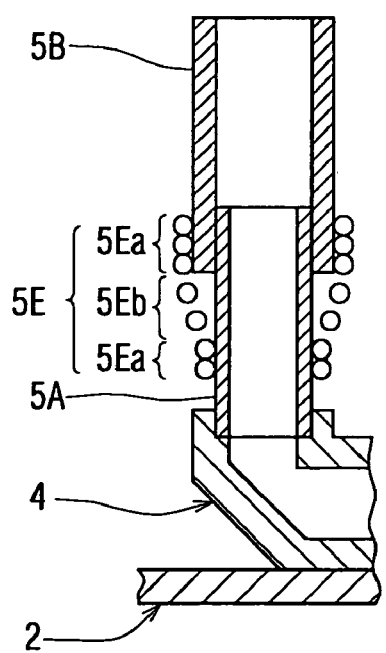
FIG. 25 is a partial sectional view of a modification to the seventh embodiment of the liquid level detecting apparatus according to the invention.

As shown in FIG. 25, a modification to the fuel liquid level detecting apparatus 1F of the seventh embodiment is such that the lower pipe 5A and upper pipe 5B in the fuel liquid level detecting apparatus 1F of the seventh embodiment are formed of tubular members which have different outside dimensions and inside diameter dimensions, and that one of the pipes is inserted into the other, whereupon a spring 5E is held in close touch with the outer periphery of the insertion part of the pipes. The other constituents of the fuel liquid level detecting apparatus 1F are constructed similarly to the corresponding constituents of the fuel liquid level detecting apparatus 1F (1C), respectively.

The lower pipe 5A and the upper pipe 5B are insertionally assembled so as to be slidable to each other. The spring 5E held in close touch with the outer periphery of the insertion part is such that both its end parts are close-coiled parts 5Ea, while its middle part is a loosely-coiled part 5Eb in the shape of a compression spring. Both the close-coiled parts 5Ea are respectively held in close touch with the lower pipe 5A and the upper pipe 5B.

In the job of attaching the fuel liquid level detecting apparatus 1F to a fuel tank 2, when a guide pipe 5 has touched the fuel tank 2, the upper pipe 5B slides relative to the lower pipe 5A while resisting the restoring force of the loosely-coiled part 5Eb of the spring 5E, thereby to move downwards in FIG. 25.

Accordingly, the same effects as in the fuel liquid level detecting apparatus 1F of the seventh embodiment are attained.

Although a step arises on the inner surface of the guide pipe 5 in the modification to the fuel liquid level detecting apparatus 1F of the seventh embodiment, it does not reflect an ultrasonic wave proceeding from a measuring reflective surface 44 toward a liquid level 81, onto the side of the measuring reflective surface 44. Accordingly, the position of the liquid level 81 is detectable at a high accuracy even in the modification to the fuel liquid level detecting apparatus 1F of the seventh embodiment.

By the way, in each of the fuel liquid level detecting apparatuses 1F–1I of the seventh–tenth embodiments, the guide pipe 4 is formed from an aluminum die casting alloy, while the guide pipe 5 is formed of a stainless steel pipe. However, the guide pipes 4 and 5 may well be formed from other substances.

Besides, in each of the fuel liquid level detecting apparatuses 1F–1I of the seventh–tenth embodiments, the measuring reflective surface 44 is shaped in a flat surface, but it may well be shaped in a concave surface which is concave facing both the ultrasonic generation surface 31 and the liquid level 81.

Besides, in each of the fuel liquid level detecting apparatuses 1F–1I of the seventh–tenth embodiments, the ultrasonic sensor 3 is installed with the ultrasonic generation direction of the ultrasonic wave held in parallel with the liquid level 81, and the guide pipe 4 is provided with the measuring reflective surface 44, thereby to reflect the ultrasonic wave toward the liquid level 81. However, the ultrasonic sensor 3 may well be installed at the lower end of the guide pipe 5, that is, at the lower end of the lower pipe 5A, by omitting the guide pipe 4 and the measuring reflective surface 44, so as to transmit the ultrasonic wave from the ultrasonic sensor 3 directly toward the liquid level 81 inside the guide pipe 5.

Besides, the guide pipe 4 is provided with the correcting reflective surface 41 in each of the fuel liquid level detecting apparatuses 1F–1I of the seventh–tenth embodiments, but the correcting reflective surface 41 need not always be formed. In this case, the liquid level 81 may well be calculated by correcting the propagation velocity of the ultrasonic wave in the fuel 8 on the basis of a temperature detection signal which is generated by an air temperature sensor (not shown) mounted in the automobile, or a temperature detection signal which is obtained by installing a fuel temperature sensor in the fuel tank 2.

(Eleventh Embodiment)

Figure 26:
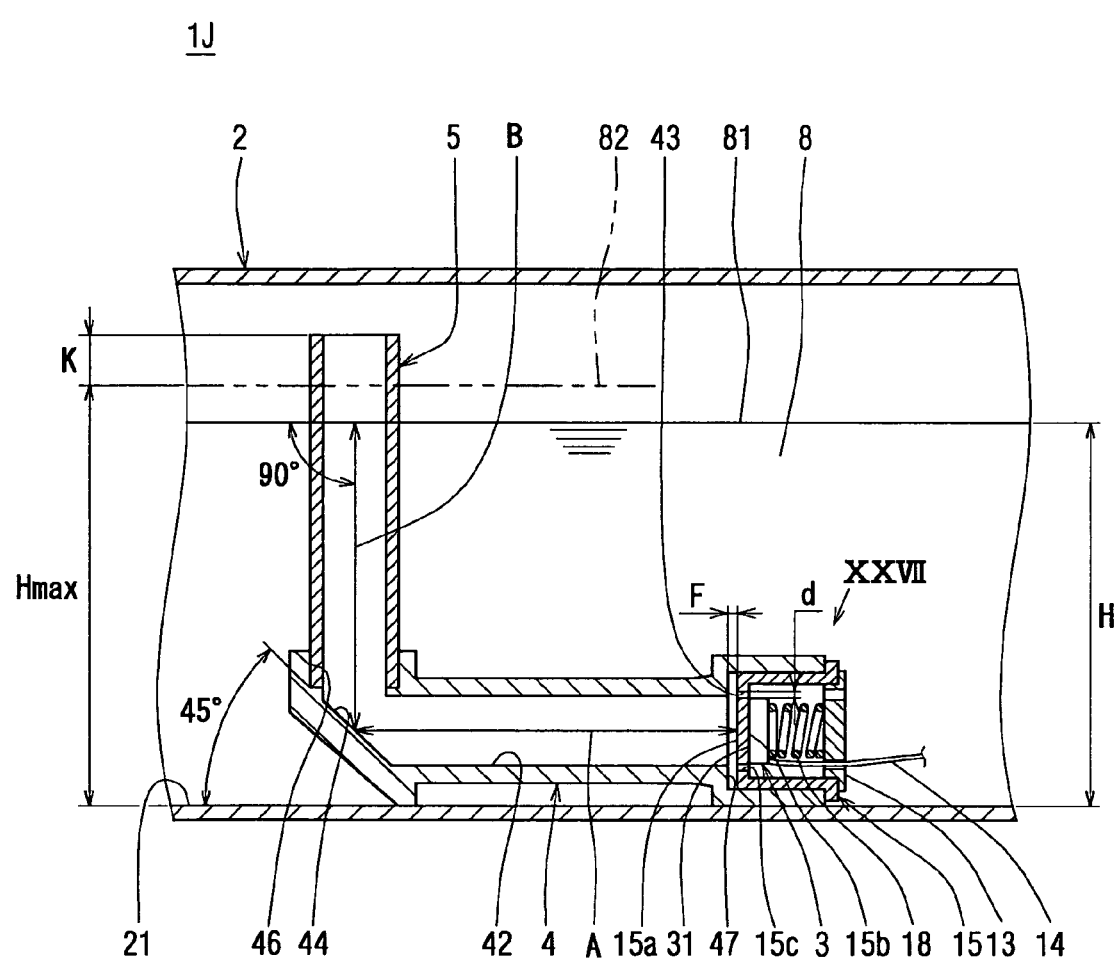
FIG. 26 is a partial sectional view of the eleventh embodiment of the liquid level detecting apparatus according to the invention.
Figure 27:
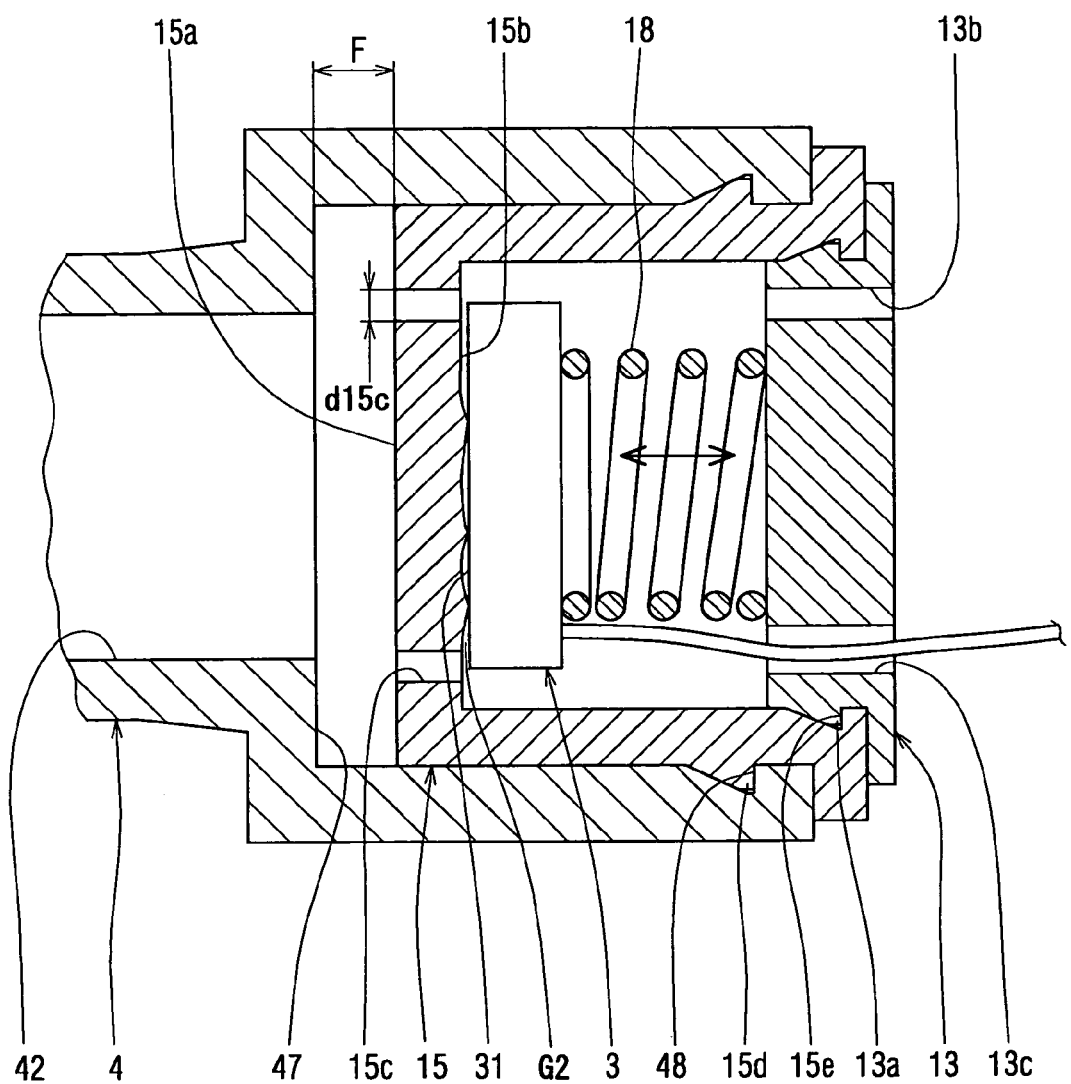
FIG. 27 is an enlarged sectional view of part XXVII in FIG. 26.
Figure 28:
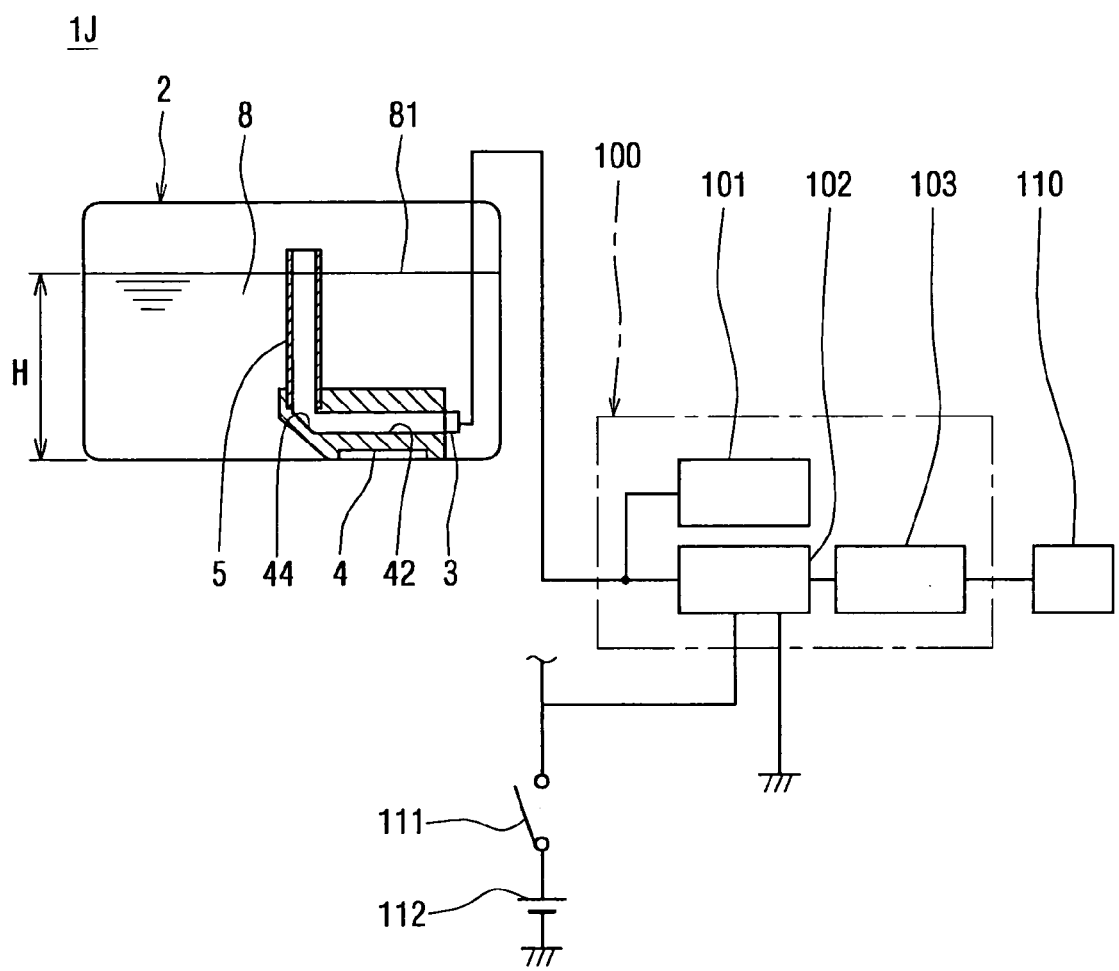
FIG. 28 is a schematic diagram showing an electric circuit arrangement in the eleventh embodiment of the liquid level detecting apparatus according to the invention.

As shown in FIGS. 26 and 27, a fuel liquid level detecting apparatus 1J in the eleventh embodiment is such that the ultrasonic sensor 3 of the fuel liquid level detecting apparatus 1B in the second embodiment is not fixed to the bottom 15b of the bracket 15 by bonding or the like, but that it is fixed by being held between the bracket 15 and the plug 13 fitted in this bracket, owing to the restoring force of a spring 18. The other constituents of the fuel liquid level detecting apparatus 1J are constructed similarly to the corresponding constituents of the fuel liquid level detecting apparatus 1B, respectively.

The ultrasonic sensor 3 is constructed similarly to the ultrasonic sensor 3 of the fuel liquid level detecting apparatus 1A in the first embodiment. The bracket 15 is formed substantially in the shape of a bottomed cylinder from a resin material or a metal material. In the bracket 15, the ultrasonic sensor 3 is located so as to have its ultrasonic generation surface 31 held in close touch with the bottom 15b of the bracket 15.

The plug 13 formed from a resin material or the like is fixed on the opposite side to the bottom 15b of the bracket 15 (right side in FIG. 26) in such a way that the protuberance 13a thereof is held in engagement with the engaging portion 15e of the bracket 15.

The spring (elastic member) 18 is interposed between the ultrasonic sensor 3 and the plug 13. This spring 18 is a coiled spring and is compressed in a state where it is assembled in the bracket 15, and the restoring force thereof acts in a direction indicated by a double-headed arrow in FIG. 27. Owing to the elastic force, the ultrasonic sensor 3 is brought into close touch with the bottom 15b of the bracket 15.

The plug 13 is provided with through holes 13b, 13c. The air having accumulated in the bracket 15 is discharged out through the through hole 13b. Besides, the lead wire 14 of the ultrasonic sensor 3 is led out of the bracket 15 through the through hole 13c.

Besides, the bracket 15 is formed with through holes 15c which communicate the front surface 15a and bottom 15b of this bracket. The through holes 15c are respectively provided in the upper and lower parts of the bracket 15 in a state where the fuel liquid level detecting apparatus 1J has been attached to a fuel tank 2. As shown in FIG. 27, the through holes 15c are open at positions which overlap the ultrasonic generation surface 31 of the ultrasonic sensor 3. Besides, the minimum distance F between the surface 47 of a guide pipe 4 and the front surface 15a of the bracket 15 is set to be greater than the diametric dimension d15c of each through hole 15c in a state where the bracket 15 has been fixed to the guide pipe 4. The bracket 15 is fixed to the guide pipe 4 in such a way that the protuberance 15d thereof is held in engagement with the engaging portion 48 of the guide pipe 4.

In the case of fixing the ultrasonic sensor to the bottom of the bracket with an adhesive, the air must be prevented from mixing into the adhesive layer between the ultrasonic sensor and the wall surface of the bracket in such a way that the viscosity, temperature and coating method of the adhesive are managed to the optima during a bonding job, and that the held attitude of the ultrasonic sensor is appropriately managed after the bonding of the adhesive till the hardening thereof. Therefore, increase in the number of man-hour and consequent increase in the cost of production are incurred.

In this regard, in the fuel liquid level detecting apparatus 1J, the ultrasonic sensor 3 is urged against and fixed to the bottom 15b of the bracket 15 by the restoring force of the spring 18 without using the adhesive or the like. Besides, the bracket 15 is provided with the through holes 15c which communicate the bottom 15b and the front surface 15a of this bracket, and a part of which overlaps the ultrasonic generation surface 31 of the ultrasonic sensor 3.

Microscopically, the ultrasonic generation surface 31 of the ultrasonic sensor 3 and the bottom 15b of the bracket 15 are not perfect flat surfaces, but they have minute ruggedness as shown in FIG. 27. Accordingly, the ultrasonic generation surface 31 and the bottom 15b are not perfectly held in close touch, but a minute gap G2 is formed between both the portions.

Immediately after the fuel liquid level detecting apparatus 1J has been attached into the fuel tank 2, the air exists in the gap between the ultrasonic generation surface 31 and the bottom 15b. When a fuel 8 has been thereafter injected into the fuel tank 2, the guide pipe 4 and the bracket 15 are immersed in the fuel 8. On this occasion, the fuel 8 fills up the guide portion 42 of the guide pipe 4, and it flows into the bracket 15 through the through holes 15c of this bracket 15 to arrive at the close touch portion between the ultrasonic generation surface 31 and the bottom 15b. The fuel 8 enters the gap G2 between the ultrasonic generation surface 31 and the bottom 15b by a capillary action until this gap G2 is completely filled up with the fuel 8.

Thus, in the close touch portion between the ultrasonic generation surface 31 and the bottom 15b, the fuel 8 intervenes except in parts at which both the portions 31 and 15b are really held in touch, so that the vibration of the ultrasonic sensor 3 is conveyed to the bracket 15 through the fuel 8, not through the air.

Accordingly, the vibration energy of the ultrasonic sensor 3 can be efficiently conveyed to the bracket 15, so that an ultrasonic wave generated from the ultrasonic sensor 3 can be transmitted into the fuel 8 at a high efficiency with the cost increases suppressed.

Besides, the through holes 15c are respectively provided in the upper and lower parts of the bracket 15.

Accordingly, when the fuel tank 2 is replenished with the fuel 8, the air having stayed in the bracket 15 is effectively discharged out of this bracket through the through holes 15c, and the gap G2 between the ultrasonic generation surface 31 and the bottom 15b is completely filled up with the fuel 8.

Besides, in the state where the bracket 15 has been fixed to the guide pipe 4, the minimum distance F between the surface 47 of the guide pipe 4 and the front surface 15a of the bracket 15 is set to be greater than the diametric dimension d15c of each through hole 15c.

In a case where the minimum distance F between the surface 47 of the guide pipe 4 and the front surface 15a of the bracket 15 is smaller than the diametric dimension d15c of each through hole 15c, and where the fuel tank 2 is replenished with the fuel 8 in a state in which the gap G2 between the ultrasonic generation surface 31 and the bottom 15b is not filled up the fuel 8, the fuel 8 enters the interspace between the surface 47 and the front surface 15a owing to the capillary action, but the fuel 8 in the interspace is drawn by surface tensions and does not enter the through holes 15c. That is, the fuel 8 does not enter the bracket 15, and the gap G2 between the ultrasonic generation surface 31 and the bottom 15b is not sufficiently filled with the fuel 8.

Since, in the fuel liquid level detecting apparatus 1J, the minimum distance F between the surface 47 of the guide pipe 4 and the front surface 15a of the bracket 15 is set to be greater than the diametric dimension d15c of each through hole 15c, the fuel 8 having entered the interspace between the surface 47 and the front surface 15a flows into the through holes 15c with ease, and the gap G2 between the ultrasonic generation surface 31 and the bottom 15b is sufficiently filled with the fuel 8.

When the fuel 8 has been consumed to substantially empty the fuel tank 2, the fuel 8 remains while filling up the guide portion 42 of the guide pipe 4, in some cases, and the air enters the guide portion 42 of the guide pipe 4 in the other cases, depending upon the shapes of the fuel tank 2. Even in the case where the air enters the guide portion 42 of the guide pipe 4, the fuel 8 which lies in the gap G2 between the ultrasonic generation surface 31 of the ultrasonic sensor 3 and the bottom 15b of the bracket 15 is still held in the gap G2 under the action of surface tensions. Besides, even in a case where the air has entered part of the gap G2 due to the jolting of an automobile, or the like, this gap G2 is completely filled up with the fuel 8 again when the fuel tank 2 is replenished with the fuel 8 to immerse the guide pipe 4 and the bracket 15 in the fuel 8.

Besides, a reflective surface 44 which reflects the ultrasonic wave generated by the ultrasonic sensor 3, toward a liquid level 81, is formed unitarily with the guide pipe 4 which defines the ultrasonic transmission route between the ultrasonic sensor 3 and this reflective surface 44. Accordingly, even in a case where the shape of the fuel tank 2 is complicated, for example, where an extent from the bottommost part of the fuel tank 2 to the highest liquid level 82, namely, the liquid level 82 corresponding to the maximum quantity of storage of the fuel 8 in the fuel tank 2 cannot be perpendicularly seen through, the liquid level 81 in the fuel tank 2 can be reliably detected from the highest liquid level 82 to the lowest liquid level by appropriately setting the position of the reflective surface 44.

(Modification to Eleventh Embodiment)

Figure 29:
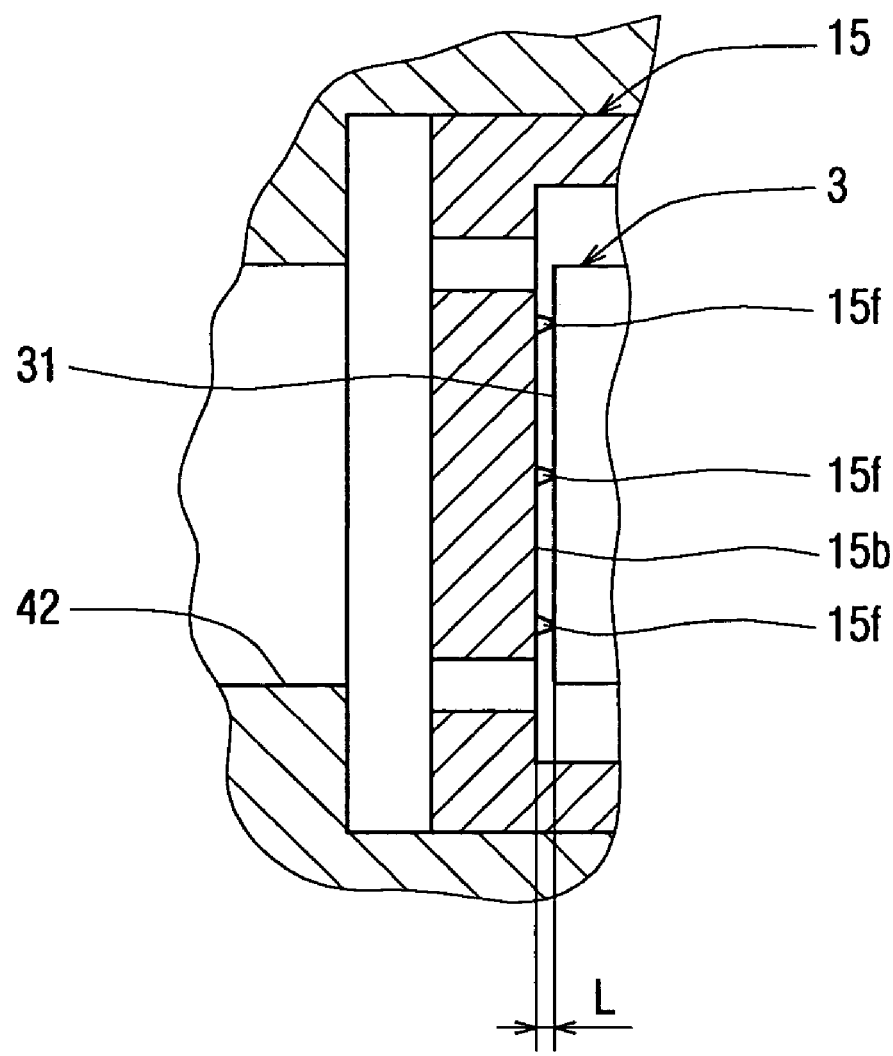
FIG. 29 is a partial sectional view of a modification to the eleventh embodiment of the liquid level detecting apparatus according to the invention.

As shown in FIG. 29, a modification to the fuel liquid level detecting apparatus 1J of the eleventh embodiment is such that the shape of the bracket 15 in the fuel liquid level detecting apparatus 1J of the eleventh embodiment is partly altered. The other constituents of the modification are constructed similarly to the corresponding constituents of the fuel liquid level detecting apparatus 1J of the eleventh embodiment, respectively.

In this modification, the bottom 15b of the bracket 15 is provided with three protuberances 15f which protrude toward the ultrasonic generation surface 31 of an ultrasonic sensor 3. The protuberances 15f are located at equiangular intervals, namely, at intervals of 120 degrees on a circumference which is concentric with the ultrasonic generation surface 31.

When the ultrasonic sensor 3 is assembled to the bracket 15, the ultrasonic generation surface 31 abuts against the three protuberances 15f, and a gap whose length is substantially equal to the height L of each protuberance 15f is defined between the ultrasonic generation surface 31 of the ultrasonic sensor 3 and the bottom 15b of the bracket 15 as shown in FIG. 29. The height L of each protuberance 15f is set at a dimension at which the interspace between the ultrasonic generation surface 31 and the bottom 15b is sufficiently filled with a fuel 8 by a capillary action.

Accordingly, the interspace between the ultrasonic generation surface 31 and the bottom 15b is sufficiently filled with the fuel 8, and the vibration energy of an ultrasonic wave generated from the ultrasonic sensor 3 can be conveyed to the bracket 15 at a high efficiency.

(Another Modification to Eleventh Embodiment)

Figure 30:
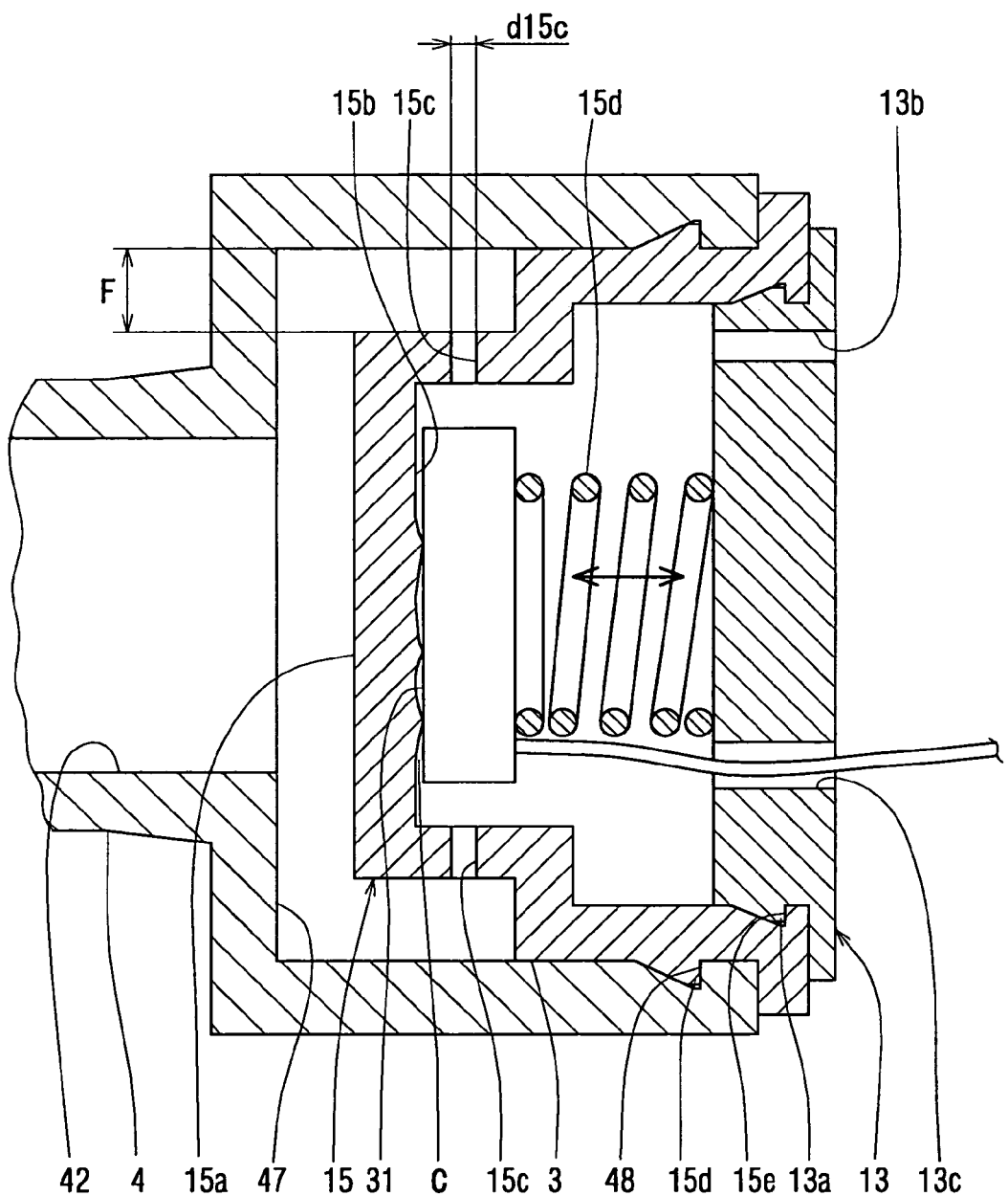
FIG. 30 is a partial sectional view of another modification to the eleventh embodiment of the liquid level detecting apparatus according to the invention.

As shown in FIG. 30, another modification to the fuel liquid level detecting apparatus 1J of the eleventh embodiment is such that the shape of the bracket 15 in the fuel liquid level detecting apparatus 1J of the eleventh embodiment is partly altered. The other constituents of the modification are constructed similarly to the corresponding constituents of the fuel liquid level detecting apparatus 1J of the eleventh embodiment, respectively.

In this modification, through holes 15c are respectively formed in the upper and lower parts of the cylindrical wall of the bracket 15. Besides, the minimum distance F between a guide pipe 4 and the outside surface of the cylindrical wall of the bracket 15 is set to be greater than the diametric dimension d15c of each through hole 15c.

Accordingly, a fuel 8 which has entered the interspace between the guide pipe 4 and the outer peripheral surface of the bracket 15 flows into the bracket 15 through the through holes 15c with ease, and a gap G2 which is defined between the ultrasonic generation surface 31 of an ultrasonic sensor 3 and the bottom 15b of the bracket 15 is filled up with the fuel 8.

Also with this construction, the interspace between the ultrasonic generation surface 31 and the bottom 15b is sufficiently filled with the fuel 8, and the vibration energy of the ultrasonic sensor 3 can be conveyed to the bracket 15 at a high efficiency.

By the way, in each of the fuel liquid level detecting apparatus 1J of the eleventh embodiment and the modifications thereof, the guide pipe 4 is formed from an aluminum die casting alloy, while the guide pipe 5 is formed of a stainless steel pipe. However, the guide pipes 4 and 5 may well be formed from other substances.

Besides, in each of the fuel liquid level detecting apparatus 1J of the eleventh embodiment and the modifications thereof, the guide pipes 4 and 5 are formed as separate members, which are assembled together, but they may well be unitarily formed as a single member.

Besides, in each of the fuel liquid level detecting apparatus 1J of the eleventh embodiment and the modifications thereof, the guide pipe 5 may well be omitted.

Besides, in each of the fuel liquid level detecting apparatus 1J of the eleventh embodiment and the modifications thereof, the reflective surface 44 is shaped in a simple flat surface, but it may well be shaped in a concave surface which is concave facing both the ultrasonic generation surface 31 and the liquid level 81.

In each of the embodiments described above, the liquid level detecting apparatus according to the invention has been exemplified as being applied to the fuel liquid level detecting apparatus for the automobile, but it may well be applied to others than the fuel liquid level detecting apparatus. More specifically, the liquid level detecting apparatus may well be applied to the liquid level detection of any other liquid used in a vehicle, for example, an engine oil, a brake fluid or a window washer liquid. Alternatively, the liquid level detecting apparatus may well be applied for detecting a liquid level in a liquid transporting tank which is installed in a liquid transporting vehicle, for example, a tank truck. Further, the liquid level detecting apparatus may well be applied for detecting a liquid level in any of various containers installed in others than the vehicle, or the liquid level of a liquid flowing within any container.

What is claimed is:

1. A liquid level detecting apparatus comprising:
    an ultrasonic sensor installed in a bottom of a tank storing a liquid and detecting a liquid level of the liquid by generating an ultrasonic wave and receiving the ultrasonic wave reflected by the liquid level;
    a reflector directing the ultrasonic wave to the liquid level;
    a first cylinder enclosing a first route transmitting the ultrasonic wave between the ultrasonic sensor and the reflector and shaped to have an internal sectional area thereof perpendicular to the first route, the area gradually decreasing toward the reflector; and
    a second cylinder enclosing a second route transmitting the ultrasonic wave between the reflector and the liquid level.

2. The liquid level detecting apparatus according to claim 1, wherein each of the first and the second cylinders has a generally round cross-sectional shape perpendicular to a longitudinal axis thereof.

3. The liquid level detecting apparatus according to claim 2, wherein a diametric dimension of an end of the first cylinder on the side of the reflector is set to be generally equal to a diametric dimension of an end of the second cylinder on the side of the reflector.

4. The liquid level detecting apparatus according to claim 3, wherein the second cylinder has a generally uniform diametric dimension over the entire length thereof.

5. The liquid level detecting apparatus according to claim 1, wherein the first and the second cylinders are made of metallic material.

6. The liquid level detecting apparatus according to claim 1, further comprising:
    a baffle plate whose lower surface is generally in parallel to and at the height of a maximum level of the liquid level, wherein at least one of the second cylinder and the baffle plate comprises a passage communicating one side of the baffle plate with another side thereof.

7. The liquid level detecting apparatus according to claim 1, wherein the first cylinder comprises a step therein reflecting the ultrasonic wave generated by the ultrasonic sensor back to the ultrasonic sensor.

* * * * *